United States Patent [19]

Wallner et al.

[11] Patent Number: 4,950,646

[45] Date of Patent: Aug. 21, 1990

[54] DNA SEQUENCES, RECOMBINANT DNA MOLECULES AND PROCESSES FOR PRODUCING HUMAN LIPOCORTIN-LIKE POLYPEPTIDES

[75] Inventors: Barbara P. Wallner, Cambridge; R. Blake Pepinsky, Watertown; Jeffrey L. Garwin, Bedford; Daniel G. Schindler, Brighton; Kuo-Sen Huang, Lexington, all of Mass.

[73] Assignee: Biogen, Inc., Cambridge, Mass.

[21] Appl. No.: 929,199

[22] Filed: Jan. 10, 1986

Related U.S. Application Data

[63] Continuation-in-part of Ser. No. 690,146, Jan. 10, 1985, Pat. No. 4,879,224, which is a continuation-in-part of Ser. No. 712,376, Mar. 15, 1985, Pat. No. 4,874,743, which is a continuation-in-part of Ser. No. 765,877, Aug. 14, 1985, abandoned, which is a continuation-in-part of Ser. No. 772,892, Sep. 5, 1985, abandoned.

[51] Int. Cl.$^5$ .................... A61K 37/02; C07K 13/00
[52] U.S. Cl. ........................................ 514/12; 530/350
[58] Field of Search ................ 536/27; 435/68, 172.3, 435/240.2, 240.4, 253, 254, 255, 320; 530/350; 514/12

[56] References Cited

U.S. PATENT DOCUMENTS

| | | | |
|---|---|---|---|
| 4,239,780 | 12/1980 | Wallach | 424/330 |
| 4,394,443 | 7/1983 | Weissman et al. | 435/6 |
| 4,530,901 | 7/1985 | Weissmann | 435/70 |
| 4,537,858 | 8/1985 | O'Sullivan et al. | 435/119 |
| 4,874,743 | 10/1989 | Wallner | 514/12 |
| 4,879,224 | 11/1989 | Wallner | 435/68 |

FOREIGN PATENT DOCUMENTS

WO86/06100 10/1986 PCT Int'l Appl. .

OTHER PUBLICATIONS

F. F. Davidson et al., "Inhibition of Phospholipase A$_2$ by 'Lipocortins' and Calpactins", *J. Biol. Chem.*, 262, pp. 1698–1705 (1987).

G. J. Blackwell et al., "Glucocorticoids Induce the Formation and Release of Anti-Inflammatory and Anti--Phospholipase Proteins into the Peritoneal Cavity of the Rat", *Br. J. Pharmac.*, 76, pp. 185–194 (1982).

P. Diamond, "Biogen Produces Recombinant Anti-Inflammatory Agent", *Genetic Engineering News*, 5, p. 12 (1985).

M. DiRosa et al., "Anti-Phospholipase Proteins", *Prostaglandins*, 28, pp. 441–442 (1984).

E. Erikson et al., "Identification of a Cellular Protein Substrate Phosphorylated by the Avian Sarcoma Virus Transforming Gene Product", *Cell*, 21, pp. 829–836 (1980).

E. Erikson et al., "Biochemical Characterization of a 34 Kilodalton Normal Cellular Substrate of pp60 and an Associated 6-Kilodalton Protein", *Mol. Gen. Biol.*, 4, pp. 77–85 (1984).

M. Errasfa et al., "The Presence of Lipocortin in Human Embryonic Skin Fibroblasts and its Regulation by Anti-Inflammatory Steroids", *Biochemica et Biophysica Acta*, 847, pp. 247–254 (1985).

(List continued on next page.)

*Primary Examiner*—Lester L. Lee
*Assistant Examiner*—Nina Ossanna
*Attorney, Agent, or Firm*—James F. Haley, Jr.; Denise L. Loring; David J. Meyer

[57] ABSTRACT

DNA sequences, recombinant DNA molecules and hosts transformed with them which produce human lipocortin-like polypeptides and methods of making and using these products. The DNA sequences and recombinant DNA molecules are characterized in that they code on expression for a human lipocortin-like polypeptide. In appropriate hosts these DNA sequences permit the production of human lipocortin-like polypeptides useful as anti-inflammatory agents and methods in the treatment of arthritic, allergic, dermatologic, ophthalmic and collagen diseases as well as other disorders involving inflammatory processes.

5 Claims, 25 Drawing Sheets

OTHER PUBLICATIONS

J. Etiene and J. Polonovski, "Phospholopase $A_2$ Activity in Rat and Human Lymphocytes", *Biochem. and Biophys. Res. Comm.*, 125, pp. 719–727 (1984).

R. Fava and S. Cohen, "Isolation of a Calcium-Dependent 35 Kilodalton Substrate for the Epidermal Growth Factor Receptor/Kinase from A-431 Cells", *J. Biol. Chem.*, 259, pp. 2636–2645 (1984).

R. J. Flower and G. J. Blackwell, "Anti-Inflammatory Steriods Induce Biosynthesis of a Phospholipase $A_2$ Inhibitor which Prevents Prostaglandin Generation", *Nature*, 278, pp. 456–459 (1979).

R. J. Flower et al., "Macrocortin and the Mechanism of Action of the Glucocorticoids", *Advances in Inflammation Research*, 7, pp. 61–70 (1984).

M. J. Geisow, "Common Domain Structure of Ca and Lipid Binding Proteins", *FEBS Letters*, 92, pp. 99–103 (1986).

M. J. Geisow and J. H. Walker, "New Proteins Involved in Cell Regulation by Ca and Phospholipids", *Trends Biochem. Sci.*, 11, pp. 420–423 (1986).

V. Gerke and K. Weber, "Identity of p36K Phosphorylated Upon Rous Sarcoma Virus Transformation with a Protein Purified from Brush Borders; Calcium-Dependent Binding to Non-Erythoid Spectrin and F-Actin", *EMBO Journal*, 3, pp. 227–233 (1984).

V. Gerke and K. Weber, "Calcium-Dependent Conformational Changes in the 36-kDa Subunit of Intestinal Protein I Related to the Cellular 36-kDa Target of Rous Sarcoma Virus Tyrosine Kinase", J. Biol. Chem., 260, pp. 1688–1695 (1985).

J. R. Glenney and B. F. Tack, "Amino-Terminal Sequence of p36 and Associated p10: Identification of the Site of Tyrosine Phosphorylation and Homology with S-100", *Proc. Nat. Acad. Sci. U.S.A.*, 82, pp. 7884–7888 (1985).

T. Hattori et al., "Inhibition of Human Natural Killer (NK) Activity and Antibody Dependent Cellular Cytotoxicity (ADCC) by Lipomodulin, a Phospholipase Inhibitory Protein", *J. Immunol.*, 131, pp. 662–665 (1983).

F. Hirata, "The Regulation of Lipomudulin, a Phospholipase Inhibitory Protein in Rabbit Neutrophils by Phosphorylation", *J. Biol. Chem.*, 256, pp. 7730–7733 (1981).

Hirata et al., "Presence of Autoantibody for Phospholipase Inhibitory Protein, Lipomudulin in Patients with Rheumatic Disease", *Proc. Nat. Acad. Sci. U.S.A.*, 78, pp. 3190–3194 (1981).

F. Hirata, "Roses of Lipmodulin: A Phospholipase Inhibitory Protein in Immunoregulation", *Adv. Inflm. Res.*, 7, pp. 71–78 (1984).

F. Hirata et al., "Inhibition of Leukocyte Chemotaxis by Glu-Glu-Glu-Glu-Tyr-Pro-Met-Glu and Leu-Ile-Glu-Asp-Asn-Glu-Tyr-Thr-Ala-Arg-Gln-Gly", *Biochemn. and Biophys. Res. Comm.*, 118, pp. 682–690 (1984).

F. Hirata et al., "Isolation and Characterizaiton of Lipocortin (Lipomodulin)", *Agents and Actions*, 17, pp. 263–266 (1985).

K. Huang et al., "Two Human 35 Kd Inhibitors of Phospholipase $A_2$ are Realted to Substrates of pp60 and of the Epidermal Growth Factory Receptor/Kinas", *Cell*, 46, pp. 191–199 (1986).

R. H. Kretsinger et al., "Consensus in Exocytosis", *Nature*, 320, p. 573 (1986).

I. Mancheva et al., "The Primary Structure of the Inhibitor of Vipoxin from the Vernom of the Bulgarian Viper (Vipera Ammodytes, Serpentes)", *Hoppe–Selye's Z. Physiol. Chem.*, 365, pp. 885–894 (1984).

I. Mancheva et al., "Sequence Homology Between Phospholipase and its Inhibitor in Snake Vernom: The Primary Structure of the Inhibitor of Vipoxin from the Vernom of the Bulgarian Viper", *Biol. Abstr.*, 79, #39874 (1984).

T. Maniatis et al., "Molecular Cloning (A Laboratory Manual), "pp. 5–6, 405–514 (1984).

J. F. Morrow, "Recombinant DNA Techniques", *Methods in Enzymology*, 68, pp. 3–24 (1979).

Oroszylan et al., "Amino-and Carboxyl-Terminal Amino Acid Sequences of Proteins Coded by gag Gene of Murine Leukemia Virus", *Proc. Nat. Acad. Sci. U.S.A.*, 75, pp. 1404–1408 (1977).

R. B. Pepinsky et al., "Localization of Lipid-Protein and Protein-Protein Interactions within the Murine gag Precursor by a Novel Peptide-Mapping Technique", *J. Biol. Chem.*, 258, pp. 11229–11235 (1983).

R. B. Pepinsky and L. K. Sinclair, "Epidermal Growth Factor-Dependent Phosphoylation of Lipcortin", *Nature*, 321, pp. 81–84 (1986).

R. B. Pepinsky et al., "Purification and Partial Sequence Analysis of a 37-kDa Protein that Inhibits Phospholi- (List continued on next page.)

OTHER PUBLICATIONS pase $A_2$ Activity from Rat Peritoneal Exudates", *J. Biol. Chem.*, 261, pp. 4239–4246 (1986).

K. Radke et al., "Transformation by Rous Sarcoma Virus: A Cellular Substrate for Transformation-Specific Protein Phosphorylation Contains Phosphotyrosine", *Cell*, 21, pp. 821–828 (1980).

C. J. M. Saris et al., "The cDNA Sequence for the Protein–Tyrosine Kinase Substrate p36 (Calpactin I Heavy Chain) Reveals a Multidomain Protein with Internal Repeats", *Cell*, 46, pp. 201–212 (1986).

B. P. Wallner et al., "Cloning and Expression of Human Lipocortin, A Phospholipase $A_2$ Inhibitor with Potential Anti-Inflammatory Activity", *Nature*, 320, pp. 77–81 (1986).

"Biogen Produces Anti-Inflammatory Agent; Davies Resigns", *Genetic Engineering Letter*, p. 4, Jun. 10, 1985.

Proc. Nat'l. Acad. Sci., 82 (1985), 7884–7888.

Cell., vol. 46, 191–199 (1986).

Chem. Abstr., vol. 100, (1984), 119189.

Chem. Abstr., vol. 99, (1983), 86478.

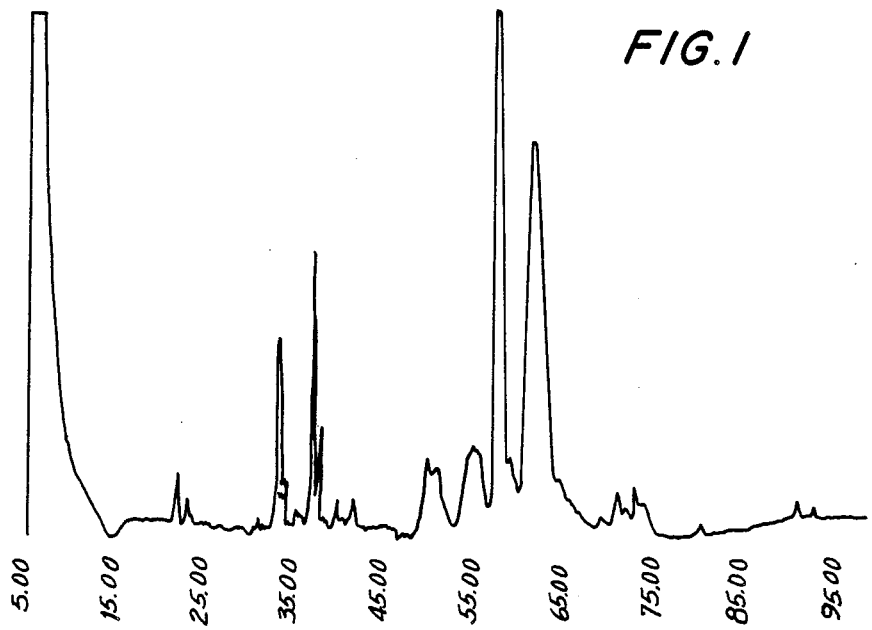

FIG.1

CNBr 1: (less than 2Kd based on amino acid analysis)

- Met - lys - gly - ala - gly - thr - arg - arg - lys - thr -
  1     2     3     4     5     6     7     8     9    10 leu - ile
  11    12

CNBr 2: (less than 2Kd based on amino acid analysis)

- met - leu - lys - thr - pro - ala - gln - phe - asp - ala -
  1     2     3     4     5     6     7     8     9     10 asp - glu - leu - ile(?) - arg(?)
  11    12    13    14       15

CNBr 3: (7 Kd based on SDS-polyacrylamide gel electrophoresis)

- met - $\frac{tyr}{lys}$ - $\frac{val}{ala}$ - asn - gln - asp - $\frac{leu}{trp}$ - ala - $\frac{ala}{gln}$ -
  1      2          3          4     5     6      7          8      9

CNBr 4: (no protein detected by SDS-PAGE)

CNBr 5: (mixture of peptides, less than 5Kd based on SDS-PAGE)

CNBr 6: (mixture consisting of two 12 Kd fragments based on SDS-PAGE)

FIG. 2

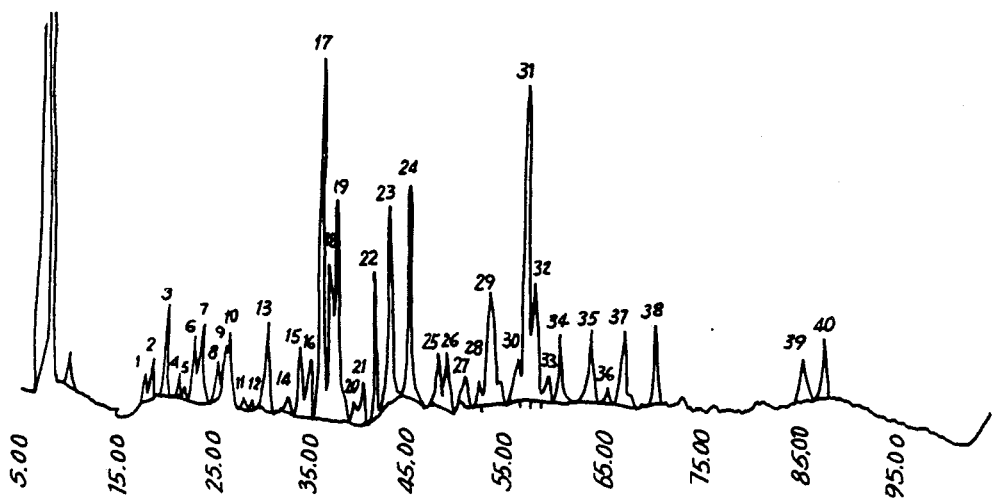

T17(a+b): $-\dfrac{ala}{tyr} - \dfrac{leu}{phe} - \dfrac{gln}{val} - \dfrac{gln}{gln} - \dfrac{ala}{lys} - \dfrac{tyr}{gly} - gln - \dfrac{arg}{gly}$
           1     2    3    4    5    6    7    8

T22(a): - ser - glu - ile - asp - met - asn - glu - ile - lys
           1    2    3    4    5    6    7    8    9

T22(b): - lys - val - phe - gln - asn - tyr - arg
           1    2    3    4    5    6    7

T23: - ser - tyr - pro - his(arg) - leu
        1    2    3    4    5

T24: - thr - pro - ala - gln - phe - asp - ala - asp - glu -
        1    2    3    4    5    6    7    8    9
       leu - leu - arg
       10   11   12

T29: - ala - ala - tyr - leu - gln - glu - thr - gly - lys -
        1    2    3    4    5    6    7    8    9
       pro - leu - asp - glu - thr - leu - lys
       10   11   12   13   14   15   16

T31: - gly - gly - pro - gly - ser - ala - val - ser - pro -
       1    2    3    4    5    6    7    8    9
       tyr - pro - ser(thr) - phe - asn - ser(thr) - ser
       10   11   12   13   14   15   16
       ser - thr - val - ala - trp - ala
       17   18   19   20   21   22

T35: - lys - gly - thr - asp - val - asn - val - phe(?) -
        1    2    3    4    5    6    7    8
       asn - thr - x - leu
       9    10   11   12

T38: - gly - leu - gly - thr - asp - glu -
        1    2    3    4    5    6

FIGURE 3

Sequence T22a:  GluIleAspMetAsnGluIle
    20-mer      GARATHGAYATGAAYGARAT

Sequence T22b:  LysValPheGlnAsnTyr
    17-mer      AARGTNTTYCARAAYTA

Sequence T24[1]: AlaGlnPheAspAlaAspGlu
    20-mer      GCNCARTTYGAYGCNGAYGA

Sequence T29:   GlnGluThrGlyLysPro
    17-mer      CARGARACNGGNAARCC

[1] The sequence shown for T24 is also contained within CNBr fragment 2.

Coding redundancies are:

```
701  ACGTAAACGTGTTCAATACCATCCTTACCACCAGAAGCTATCCACAACTTCGCAGAGTGTTCAGAAATACACCAAGTACAGTAAGCATGACATGAACAA    800
     ----------------------------------------------------------------------------------------------------
     TGCATTGCACAAGTTATGGTAGGAATGGTGGTCTTCGATAGGTGTTGAAGCCTCTCACAAAGTCTTTATGTGGTTCATGTCATTCGTACTGTACTTGTT
     spValAsnValPheAsnThrIleLeuThrArgSerTyrProGlnLeuArgArgValPheGlnLysTyrThrLysTyrSerLysHisAspMetAsnLy

801  AGTTCTCGACCTGGAGTTGAAAGGTGACATTGAGAAATGCCTCACAGCTATCGTGAAGTGCCCACAAGCAAACCAGCTTTCTTTGCAGAGAAGCTTCAT    900
     ----------------------------------------------------------------------------------------------------
     TCAAGACCTGGACCTCAACTTCCACTGTAACTCTTTACGGAGTGTCGATAGCACTTCACGCGGTGTCGTTGGTCGAAAGAAACTCTCTTCGAAGTA
     sValLeuAspLeuGluLeuLysGlyAspIleGluLeuLysCysLeuThrAlaIleValLysCysAlaThrSerLysProAlaPhePheAlaGluLysLeuHis

901  CAAGCCATGAAAGGTGTTGGAACTCGCCATAAGGCATTGATCAGGATTATGGTTTCCCGTTCTGAAATTGACATGAATATCAAAGCATTCTATCAGA   1000
     ----------------------------------------------------------------------------------------------------
     GTTCGGTACTTTCCACAACCTTGAGCGGTATTCCGTAACTAGTCCTAATACCAAAGGGCAAGACTTAACTGTACTACTATAGTTTCGTAAGATAGTCT
     GlnAlaMetLysGlyValGlyThrArgHisLysAlaLeuIleArgIleMetValSerArgSerGluIleAspMetAsnAspIleLysAlaPheTyrGlnL

1001 AGATGTATGGTATCTCCCTTTGCCAAGCCATCCTGGATGAAACCAAAGGAGATTATGAGAAAATCCTGGTGGCTCTTTGTGGAGAAACTAAACATTCCC   1100
     ----------------------------------------------------------------------------------------------------
     TCTACATACCATAGAGGGAAACGGTTCGGTAGGACCTACTTGGTTTCCTCTAATACTCTTTAGGACCACCGAGAAACACCTCCTTGATTTGTAAGGG
     ysMetTyrGlyIleSerLeuCysGlnAlaIleLeuAspGlyThrLysGlyAspTyrGluLysIleLeuValAlaLeuCysGlyAsnEnd
                                                                                              346

1101 TTGATGGTCTCAAGCTATGATCAGAAGACTTTAATTATATATTTCATCCTATAAGCTTAAATAGGAAAGTTTCTTCAACAGGATTACAGTGTAGCTACC   1200
     ----------------------------------------------------------------------------------------------------
     AACTACCAGAGTTCGATACTAGTCTTCTGAAATTTAAATCATTTTATAAAATTAATATAATATATATAACTCTGTAATAAGAGATAAGTCCATTTTTAAAAATGTTTCCTAATGTCACATCGATGG

1201 TACATGCTGAAAAATATAGCCTTTAAATCGGAAATTTAGTAACATAAATATATAATATATATATTTCAGTTAAAAATGTTTTCCCCAAACCATAAAA   1300
     ----------------------------------------------------------------------------------------------------
     ATGTACGACTTTTTATATCGGAAATTTAGTAAAATATTTGAGACATATTATCTCTATTCAGTTAAAAATTTTTTACAAAAGGGGTTTGGTATTTT

1301 CCCTATACAAGTGTTCTAGTAACAATACATGAGAAAGATGTCTATGTAGCTGAAATAAAATGACGTCACAAGAC                          1376
     ----------------------------------------------------------------
     GGGATATGTTCAACAAGATCATTGTTATGTACTCTTCTACAGATACATCGACTTTTATTTTACTGCAGTGTTCTG
```

25.00  ─ GDYEK
       ─ GDIEK
       ─ QQIK
       ─ RVFOK
35.00  ─ LHQAMK
       ─ AFYQK
       ─ IMVSR
       ─ ALVEAGER
       ─ DITSDTSGDF R
       ─ SYPQLR
       ─ ALYEAGERR K
       ─ SEIDMNDIK
45.00  ─ VYREELK
       ─ TPAQFDADEL R

─ NALLSLAK
       ─ AAYLQETGKPLDETLK
55.00  ─ QAWFIENEEQ EYVQTVK
       ─ GGPGSAVSPY PTFNPSSDVA ALHK
       ─ MAMVSEFLK  MAMVSEFLKQAWFIENEEQ EYVQTVK
       ─ GTDVNVFNTI LTTR
       ─ KGTDVNVFNTI LTTR
65.00  ─ CLTAIVK
       ─ GVDEATIIDI LTK
       ─ GLGTDEDTLI EILASR 75.00

LIST OF OLIGONUCLEOTIDES

| Lipo-60 | CGTGCTGCCCTGAAAGGCCTTGG | Met 127→ Leu |
| --- | --- | --- |
| Lipo-61 | AAGGCAATATTGGTTAAAGGT | Met 56→ Leu |
| Lipo-68 | GGAGGTTGTTATGGCTCTGCTA | Leu 109→ Met |
| Lipo-75 | GATCTGGCCAAAGATATCATG | Thr 169→ Met by |
| Lipo-76 | GATCCATGATATCTTTGGCCA | insertion |
| Lipo-77 | GTCATCCACCATGGGTCCCGGA | Gly 30→ Met |
| Lipo-78 | TCTGAATCGGCCATGTCTTCAT | Leu 198→ Met |
| Lipo-79 | ATACCATCATGACCACCAG | Leu 225→ Met |

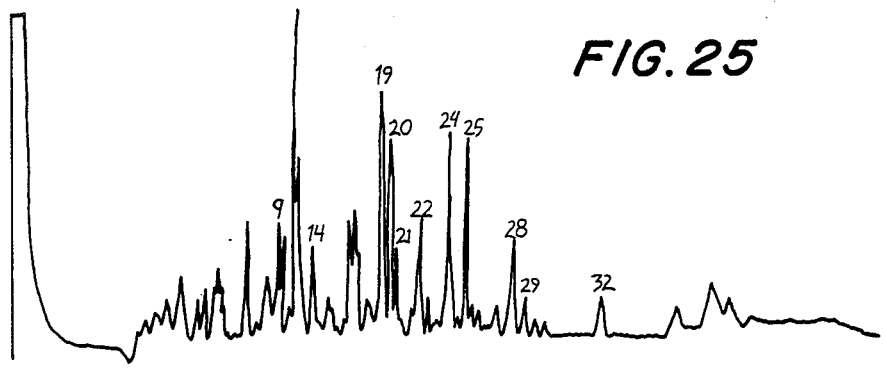

FIG. 25

```
            1     2     3     4     5     6
T9:      - Leu - Tyr - Asp - Ser - Met - Lys -

1     2     3     4     5     6     7
T14:     - Ser - Glu - Ile - Asp - Met - Leu - Lys -
           Val   Leu   Val 1     2     3     4     5     6     7     8     9    10    11
T19:     - Leu - Ser - Leu - Asn - Gly - Asp - Thr - Ser - Thr - Pro - Pro -
                       12    13    14    15
                      Ser - Ala - Tyr - Gly -

1     2     3     4     5     6     7     8     9    10    11
T20:     - Ser - Leu - Tyr - Tyr - Tyr - Ile - Gln - Gln - Asp - Thr - Lys -

1     2     3     4     5     6     7     8     9    10    11
T21:     -  x  -  x  -  x  -  x  - Leu - Val - Lys - Gln - Tyr - Glu - Leu -
                                         Gly   Ala   Gln   Asp
                                         Ser   Lys   Val   Lys
                       12    13    14    15
                      Lys - Lys - Gln - Gln
                                        Leu 1     2     3     4     5     6     7     8     9    10    11
T22:     - Lys - Ala - Glu - Asp - Gly - Leu - Val - Ile - Asp - Tyr - Glu -
           Arg   Leu   Met   Val   Ala   Ser   Ala   Lys
                       12    13    14    15
                      Leu - Ile - Asp - Gln -

1     2     3     4     5     6     7     8
T24:     - Trp - Ile - Ser - Ile - Met - Thr - Glu - Arg -

1     2     3     4     5     6     7     8     9    10    11
T25:     - Ser - Tyr - Ser - Pro - Tyr - Asp - Met - Leu - Glu - Ser - Ile -

1     2     3     4     5     6     7     8     9    10    11
T28:     - Leu - Leu - Val - Val - Tyr - Pro -  x  - Thr - Gln - Ile - Leu -

1     2     3     4     5     6     7     8     9    10    11
T29:     - Gly - Val - Gly - Glu - Ala - Thr - Ile - Ile - Asp - Ile - Leu -
           Ala   Leu   Asp   Thr   Asp   Glu   Asp   Gly   Leu   Ile   Glu
           Asp         Leu         Tyr         Leu         Gly   Ser         Leu
                       12    13
                      Thr - Lys -
                       Ile
                       Glu 1     2     3     4     5     6     7     8     9
T32:     - Ala - Leu - Leu - Tyr - Leu -  x  - Gly - Gly - Asp -
           Gly
```

FIGURE 26

Sequence T20: SerLeuTyrTyrTyrIleGlnGlnAspThrLys

NLip1
    RTC YTG YTG GAT RTA RTA RTA YTT
    NLip2
    RTC YTG YTG AAT RTA RTA RTA YTT
    NLip3
    RTCYTG YTG TAT RTA RTA RTA YTT

Sequence T25: SerTyrSerProTyrAspMetLeuGluSerIle

NLip4
    YTC NAR CAT RTC RTC CGG
    NLip5
    YTC NAR CAT RTC RTA AGG
    NLip6
    YTC NAR CAT RTC RTA TGG
    NLip7
    YTC NAR CAT RTC RTA GGG

Sequence T24: TrpIleSerIleMetThrGluArg

NLip8
    TCA GTC ATX ATN PNX ATC CA
    NLip9
    TCG GTC ATX ATN PNX ATC CA
    NLip10
    TCC GTC ATX ATN PNX ATC CA
    NLip11
    TCT GTC ATX ATN PNX ATC CA

Sequence T9: LeuTyrAspSerMetLys

NLip12
    YTT CAT NPZ RTC RTA AA
    NLip13
    YTT CAT NPZ RTC RTA GA
    NLip14
    YTT CAT NPZ RTC RTA CA
    NLip15
    YTT CAT NPZ RTC RTA TA

FIGURE 27 cDNA insert of pNlip1

```
  1  GAATTCAAGA GAAAGTACGG CAAGTCCCTG TACTATTATA TCCAGCAAGA
 51  CACTAAGGGC GACTACCAGA AAGCGCTGCT GTACCTGTGT GGTGGAGATG
101  ACTGAAGCCC GACACGGCCT GAGCGTCCAG AAATGGTGCT CACCATGCTT
151  CCAGCTAACA GGTCTAGAAA ACCAGCTTGC GAATAACAGT CCCCGTGGCC
201  ATCCCTGTGA GGGTGACGTT AGCATTACCC CCAACCTCAT TTTAGTTGCC
251  TAAGCATTGC CTGGCCTTCC TGTCTAGTCT CTCCTGTAAG CCAAAGAAAT
301  GAACATTCCA AGGAGTTGGA AGTGAAGTCT ATGATGTGAA ACACTTTGCC
351  TCCTGTGTAC TGTGTCATAA ACAGATGAAT AAACTGAATT TGTACTTAA
     AAAAAAAAAA ........
```

Figure 28

```
N-lipocortin:    1 ........................................GAATTCAAGA   10
                                                             | |||
lipocortin  :  951 GGTTTCCCGTTCTGAAATTGACATGAATGATATCAAAGCATTCTATCAGA 1000

11 GAAAGTACGGCAAGTCCCTGTACTATTATATCCAGCAAGACACTAAGGGC   60
                 || ||||| | ||||||| |||| |||||||||||  ||  | ||||| |
            1001 AGATGTATGGTATCTCCCTTTGCCAAGCCATCCTGGATGAAACCAAAGGA 1050
                                                              x
              61 GACTACCAGAAAGCGCTGCTGTACCTGTGTGGTGGAGATGACTGAAGCCC  110
                 || |  |||||| ||| | || ||||||  |||  ||| |||| ||| |
            1051 GATTATGAGAAAATCCTGGTGGCTCTTTGTGGAGGAAACTAAACATTCCC 1100

111 GACACGGCCTGA....GCGTCCAGAAATGGTGCTCACCATGCTTCCAGCT  156
                 | | ||| |||     | |||||| |||| || || | |  |||||| |
            1101 TTGATGGTCTCAAGCTATGATCAGAAGACTTTAATTATATATTTTCATCC 1150

157 AACAGGTCTAGAAAACCAGCTTGCGAATAACAG...TCCCCGTGGCCATC  203
                 || |||| || ||| | ||| | | ||| |||   |   |||| ||| |
            1151 TATAAGCTTAAATAGGAAAGTTTCTTCAACAGGATTACAGTGTAGCTACC 1200

204 CCTGTGAGGGTGACGTTAGCATTACCCCCAACCTCATTTTAGTTGCCTAA  253
                 | ||| |  |  |  |||||||  |  |   ||||||   |||| ||
            1201 TACATGCTGAAAAATATAGCCTTTAAATCATTTTTATATTATAACTCTGT 1250

254 GCATTGCCTGGCCTTCCTGTCTAGTCTCTCCTGTAAGCCAAAGAAATGAA  303
                  |||| || || ||  |  | |||| |||||||  |   ||| |||
            1251 ATAATAGAGATAAGTCCATTTTTTAAAAATGTTTTCCCCAAACCATAAAA 1300

304 CATTCCAAGGAGTTGGAAGTGAAGTCTATGATGTGAAACACTTTGCCTCC  353
                 | |    |  | | | || ||| |||||| |||||      |||
            1301 CCCT.ATACAAGTTGTTCTAGTAACAATACATGAGAAAGATGT......C 1343

354 TGTGTACTGTGTCATAAACAGATGAATAAACTGAATTTGTACTTT 398
                 | |||| ||||     ||||  |||||||  |||   |||
            1344 TATGTAGCTGAAAATAAAATGACGTCACAAGAC............ 1376
```

DNA SEQUENCES, RECOMBINANT DNA MOLECULES AND PROCESSES FOR PRODUCING HUMAN LIPOCORTIN-LIKE POLYPEPTIDES

This is a continuation-in-part of Ser. No. 690,146, filed Jan. 10, 1985, now Pat. No. 4,879,224 and Ser. No. 712,376, filed Mar. 15, 1985 now Pat. No. 4,874,743 and Ser. No. 765,877, filed Aug. 14, 1985, now abandoned and Ser. No. 772,892, filed Sept. 5, 1985, now abandoned.

TECHNICAL FIELD OF THE INVENTION

This invention relates to DNA sequences, recombinant DNA molecules and processes for producing at least one human lipocortin.* More particularly, the invention relates to DNA sequences and recombinant DNA molecules that are characterized in that they code for at least one human lipocortin-like polypeptide. Accordingly, hosts transformed with these sequences may be employed in the processes of this invention to produce the human lipocortin-like polypeptides of this invention. These polypeptides possess anti-inflammatory activity and are useful in the treatment of arthritic, allergic, dermatologic, ophthalmic and collagen diseases.

*Lipocortin is also referred to as phospholipase inhibitor protein. Applicants used the term phospholipase inhibitor protein to refer to lipocortin in patent applications Ser. Nos. 712,376 and 690,146.

BACKGROUND OF THE INVENTION

Arachidonic acid is an unsaturated fatty acid that is a precursor in the synthesis of compounds, such as prostaglandins, hydroxy-acids and leukotrines, that are involved in inflammation reactions. It is released from membrane phospholipids by phospholipase $A_2$ activity. In response to anti-inflammatory agents, such as glucocorticoids, certain cells release proteins that have been characterized in vitro by their ability to inhibit phospholipase $A_2$. Accordingly, by inhibiting arachidonic acid production, lipocortins block the synthesis of prostaglandins and other inflammatory substances, thereby reducing inflammation [F. Hirata et al., "A Phospholipase $A_2$ Inhibitory Protein In Rabbit Neutrophils Induced By Glucocorticoids", *Proc. Natl. Acad. Sci. U.S.A.*, 77, No. 5, pp. 2533–36 (1980)].

To date, several phospholipase $A_2$ inhibitory proteins have been studied. One of them—lipomodulin—has been characterized as an about 40,000 molecular weight protein that is probably degraded by proteases in the cell to two smaller active species of about 30,000 and 15,000 molecular weight [F. Hirata et al., "Identification Of Several Species Of Phospholipase Inhibitory Protein(s) By Radioimmunoassay For Lipomodulin", *Biochem. Biophys. Res. Commun.*, 109, No. 1, pp. 223–30 (1982)]. Other experimental evidence suggests that two other phospholipase $A_2$ inhibitors, macrocortin (about 15,000 molecular weight) and renocortin (two species with molecular weights of about 15,000 and 30,000 respectively) may also be cleavage products of larger inhibitory proteins such as lipomodulin [J. F. Cloix et al., "Characterization And Partial Purification Of Renocortins: Two Polypeptides Formed In Renal Cells Causing The Anti-Phospholipase-like Action Of Glucocorticoids", *Br. J. Pharmac.*, 79. pp. 313–21 (1983); G. J. Blackwell et al., "Macrocortin: A Polypeptide Causing The Anti-Phospholipase Effect Of Glucocorticoids", *Nature*, 287, pp. 147–49 (1980)].

Although lipomodulin has been isolated from rabbit neutrophil cells, macrocortin from rat macrophages and renocortin from rat renomedullary interstitial cells, the three proteins exhibit similar biological activities, molecular weights and cross-reactivity with monoclonal antibodies against lipomodulin or macrocortin. Moreover, all are induced by glucocorticoids. Thus, it has been suggested that these phospholipase inhibitory proteins, or lipocortins, are closely related to each other and are produced by cells as a general physiological mechanism of steroid action [B. Rothhut et al., "Further Characterization Of The Glucocorticoid-Induced Antiphospholipase Protein 'Renocortin'", *Biochem. Biophys. Res. Commun.*, 117, No. 3, pp. 878–84 (1983)].

Recent data have also indicated that the 15,000 molecular weight species of lipomodulin is produced by lymphocytes in response to immunogens and acts as a glycosylation-inhibiting factor, inhibiting the glycosylation of IgE-binding factors and leading to the suppression of the IgE response [T. Uede et al., "Modulation Of The Biologic Activities Of IgE-Binding Factors: I. Identification Of Glycosylation-Inhibitory Factor As A Fragment Of Lipomodulin", *J. Immunol.*, 130, No. 2, pp. 878–84 (1983)].

As a result of their anti-inflammatory activities, lipocortins are useful for the treatment of disorders involving inflammatory processes. Such disorders include arthritic, allergic, dermatologic, ophthalmic and collagen diseases. Furthermore, the use of these proteins to treat inflammation might avoid the disadvantages now associated with present anti-inflammatory compounds.

At present two classes of compounds are being used for anti-inflammatory therapy: corticosteroids and non-steroidal anti-inflammatory drugs. Corticosteroids are generally disfavored due to the severe side effects that may be associated with their use. These effects include hypertension, gastrointestinal bleeding, muscle weakness, cataracts and convulsions. Thus, nonsteroidal anti-inflammatory compounds are preferred. However, these non-steroids may also produce side effects, such as adverse effects on gastric and platelet physiology and on the central nervous system and hematopoiesis. In addition, most non-steroidal anti-inflammatory agents inhibit the production of inflammatory substances via their effect on only one of the two pathways for production of those substances, i.e., either the cyclooxygenase pathway or the lipoxygenase pathway.

In contrast, lipocortins inhibit the production of inflammatory substances via both pathways. Furthermore, because lipocortins are only mediators of steroid action, it is unlikely that they will produce the side effects often associated with the use of corticosteroids. And because these inhibitor proteins are natural mediators produced by the cell, they are unlikely to have the side effects usually associated with many non-steroid anti-inflammatories.

In addition, lipocortin may affect inflammation through an alternate pathway by blocking the chemotactic response of leukocytes. It has been shown that certain peptides whose sequences code for the tyrosine phosphorylation sites found within pp60 src and MT antigen, i.e., the src peptide and the MT peptide, inhibit chemotaxis of rabbit neutrophils stimulated by a chemoattractant [F. Hirata et al., "Inhibition Of Leukocyte Chemotaxis By Glu-Glu-Glu-Glu-Tyr-Pro-Met-Glu And Leu-Ile-Glu-Asp-Asn-Glu-Tyr-Thr-Ala-Arg-Gln-Gly", *Biochem. Biophys. Res. Comm.*, 18, pp. 682–90 (1984)]. Lipocortin contains a similar sequence within its amino acid sequence (GluAsnGluGluGlnGluTyr, residue number 15–21). Therefore, lipocortin may exert its anti-inflammatory effect via this sequence by inhibiting or blocking the movement of neutrophils and macrophages into inflammed tissue.

To date, however, human lipocortins have not been purified from cells. Furthermore, even if a procedure could be developed for the purification of lipocortins, it is doubtful that sufficient quantities of them could be produced for their many clinical and commercial applications. Accordingly, processes enabling the production of human lipocortins in clinically useful amounts would be highly advantageous in anti-inflammatory therapy.

SUMMARY OF THE INVENTION

The present invention solves the problems referred to above by providing DNA sequences coding for at least one human lipocortin-like polypeptide and processes for producing such polypeptides in hosts transformed with those DNA sequences.

The DNA sequences of this invention are selected from the group consisting of the cDNA inserts of λLC and λNLipo21-2, DNA sequences which hybridize to these cDNA inserts and which code on expression for a human lipocortin-like polypeptide, and DNA sequences which code on expression for a polypeptide coded for on expression by any of the foregoing DNA sequences. Recombinant DNA molecules containing these DNA sequences, hosts transformed with them and human lipocortin-like polypeptides coded for on expression by them are also part of this invention.

The DNA sequences, recombinant DNA molecules, hosts and processes of this invention enable the production of human lipocortin-like polypeptides for use in the treatment of arthritic, allergic, dermatologic, ophthalmic and collagen diseases, as well as other diseases, involving inflammation processes.

BRIEF DESCRIPTION OF THE DRAWINGS

FIG. 1 depicts the amino acid sequences of fragments obtained from a cyanogen bromide digestion of rat phospholipase $A_2$ inhibitor protein.

FIG. 2 depicts the amino acid sequences of fragments obtained from tryptic digestion of rat phospholipase $A_2$ inhibitor protein.

FIG. 3 shows the four pools of chemically synthesized oligonucleotide DNA probes used to screen for the lipocortin DNA sequences of the invention.

FIG. 4 displays the nucleotide sequence of the cDNA insert of λLC which codes for human lipocortin. The figure also depicts the predicted amino acid sequence of the lipocortin protein. The numbers indicated below the amino acid sequence (e.g., 1, 30 and 346) represent the first, thirtieth and last amino acids of the protein based upon the coding sequence of the gene.

FIG. 16 depicts the amino acid sequences of fragments obtained from tryptic digestion of human lipocortin-like polypeptide.

FIG. 20 depicts the mutagenic oligonucleotides utilized according to the methods of this invention for the production of biologically active lipocortin-like polypeptide fragments by recombinant DNA techniques.

FIG. 25 depicts the tryptic map of the N-lipocortin of the invention and correlates the peaks of the map with the amino acid sequences of peptide fragments contained in those peaks.

FIG. 26 depicts the four pools of chemically synthesized oligonucleotide DNA probes used to screen for the N-lipocortin DNA sequences of the invention.

FIG. 27 displays the nucleotide sequence of the cDNA insert of pNLipl.

FIG. 28 compares the nucleotide sequence of lipocortin and the N-lipocortin cDNA sequences of this invention. The "X" on the figure indicates the end of the coding sequence and the start of the 3' non-coding sequence of the genes.

DETAILED DESCRIPTION OF THE INVENTION

Figure 5:
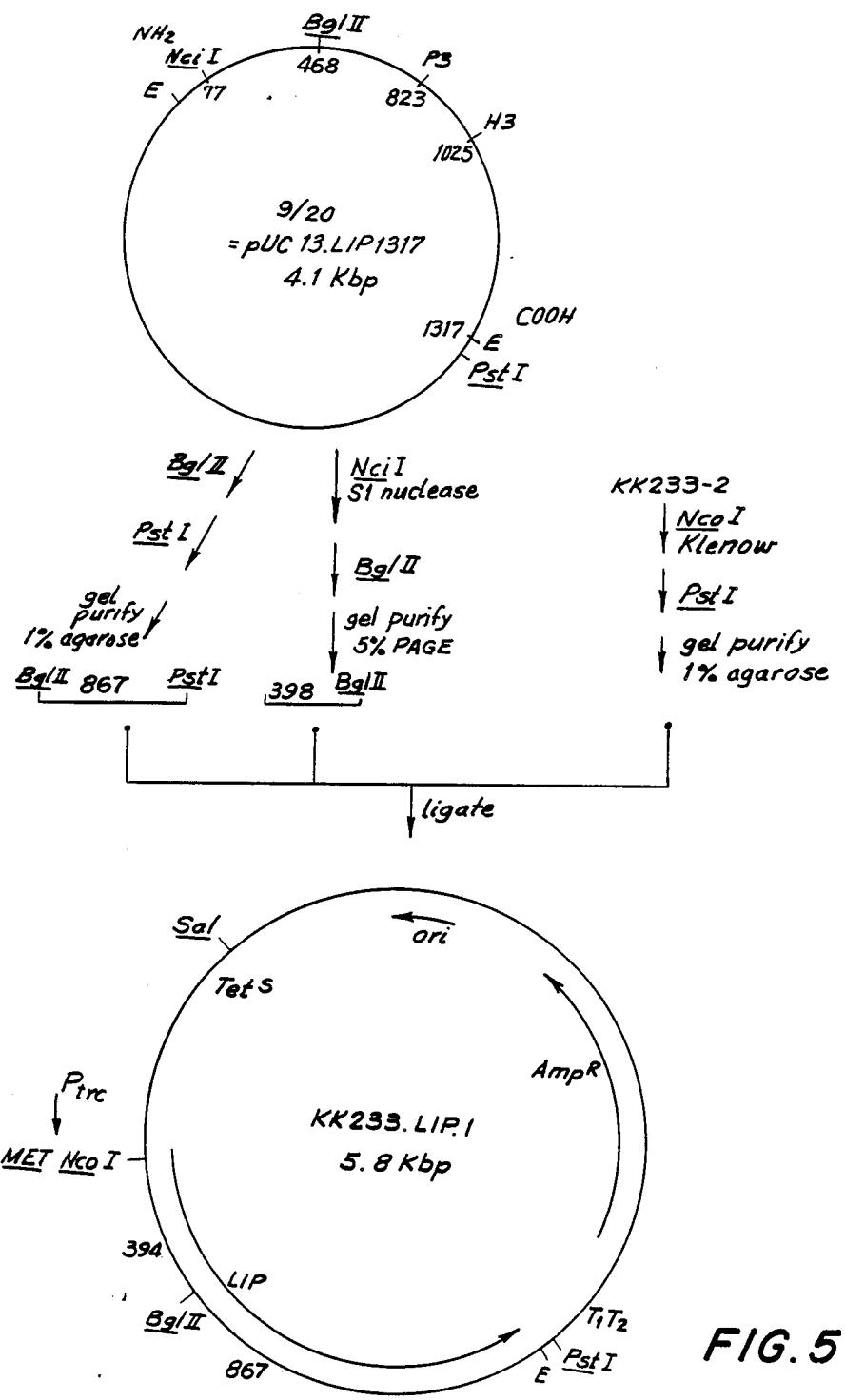
FIG. 5 depicts in schematic outline the construction of plasmid pKK233.LIP.1 used to express in one embodiment the DNA sequences of the invention.

In order that the invention herein described may be more fully understood, the following detailed description is set forth.

In the description the following terms are employed:

Nucleotide—A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is called a nucleoside. The base characterizes the nucleotide. The four DNA bases are adenine ("A"), guanine ("G"), cytosine ("C"), and thymine ("T"). The four RNA bases are A, G, C, and uracil ("U").

DNA Sequence—A linear array of nucleotides connected one to the other by phosphodiester bonds between the 3' and 5' carbons of adjacent pentoses.

Codon—A DNA sequence of three nucleotides (a triplet) which encodes through mRNA an amino acid, a translation start signal or a translation termination signal. For example, the nucleotide triplets TTA, TTG, CTT, CTC, CTA and CTG encode for the amino acid leucine ("Leu"), TAG, TAA and TGA are translation stop signals and ATG is a translation start signal.

Reading Frame—The grouping of codons during the translation of mRNA into amino acid sequences. During translation the proper reading frame must be maintained. For example, the DNA sequence GCTGGTTGTAAG may be expressed in three reading frames or phases, each of which affords a different amino acid sequence:

GCT GGT TGT AAG—Ala-Gly-CysLys
G CTG GTT GTA AG—Leu-Val-Val
GC TGG TTG TAA G—Trp-Leu-(STOP)

Polypeptide—A linear array of amino acids connected one to the other by peptide bonds between the α-amino and carboxy groups of adjacent amino acids.

Peptidase—An enzyme which hydrolyzes peptide bonds.

Genome—The entire DNA of a cell or a virus. It includes inter alia the structural gene coding for the polypeptides of the substance, as well as operator, promoter and ribosome binding and interaction sequences, including sequences such as the ShineDalgarno sequences.

Gene—A DNA sequence which encodes through its template or messenger RNA ("mRNA") a sequence of amino acids characteristic of a specific polypeptide.

Transcription—The process of producing mRNA from a gene or DNA sequence.

Translation—The process of producing a polypeptide from mRNA.

Expression—The process undergone by a gene or DNA sequence to produce a polypeptide. It is a combination of transcription and translation.

Plasmid—A nonchromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance ($TET^R$) transforms a cell previously sensitive to tetracycline into one which is resistant to it. A cell transformed by a plasmid is called a "transformant".

Phage or Bacteriophage—Bacterial virus many of which consist of DNA sequences encapsidated in a protein envelope or coat ("capsid").

Cosmid—A plasmid containing the cohesive end ("cos") site of bacteriophage λ. Cosmids may, because of the presence of the cos site, be packaged into λ coat protein and used to infect an appropriate host. Because of their capacity for large fragments of foreign DNA, cosmids are useful as cloning vehicles.

Cloning Vehicle—A plasmid, phage DNA, cosmid or other DNA sequence which is able to replicate in a host cell, characterized by one or a small number of endonuclease recognition sites at which such DNA sequences may be cut in a determinable fashion without attendant loss of an essential biological function of the DNA, e.g., replication, production of coat proteins or loss of promoter or binding sites, and which contain a marker suitable for use in the identification of transformed cells, e.g., tetracycline resistance or ampicillin resistance. A cloning vehicle is often called a vector.

Cloning—The process of obtaining a population of organisms or DNA sequences derived from one such organism or sequence by asexual reproduction.

Recombinant DNA Molecule or Hybrid DNA—A molecule consisting of segments of DNA from different genomes which have been joined end-to-end outside of living cells and able to be maintained in living cells.

Expression Control Sequence—A sequence of nucleotides that controls and regulates expression of genes when operatively linked to those genes. They include the lac system, the β-lactamase system, the trp system, the tac and trc systems, the major operator and promoter regions of phage λ, the control region of fd coat protein, the early and late promoters of SV40, promoters derived from polyoma virus and adenovirus, metallothionine promoters, the promoter for 3-phosphoglycerate kinase or other glycolytic enzymes, the promoters of acid phosphatase, e.g., Pho5, the promoters of the yeast α-mating factors, and other sequences known to control the expression of genes of prokaryotic or eukaryotic cells and their viruses or combinations thereof. For mammalian cells the gene can be linked to a eukaryotic promoter such as that for the SV40 early region coupled to the gene encoding dihydrofolate reductase and selectively amplified in Chinese hamster ovary cells to produce a cell line containing many copies of actively transcribed eukaryotic genes.

Lipocortin-Like Polypeptide—A polypeptide displaying a biological or immunological activity of a lipocortin. This polypeptide may include amino acids in addition to those of a native lipocortin or it may not include all of the amino acids of native lipocortin. Finally, it may include an N-terminal methionine. Lipocortin is also referred to as phospholipase inhibitor protein.

The present invention relates to DNA sequences and recombinant DNA molecules coding for human lipocortin-like polypeptides and processes for the production of those polypeptides.

Although a variety of selection and DNA cloning techniques might potentially have been employed in our isolating and cloning of a DNA sequence of this invention, in one embodiment of the invention, we adopted a selection strategy based upon rat phospholipase $A_2$ inhibitor protein. Accordingly, we purified a rat phospholipase $A_2$ inhibitor protein from the extracellular supernatant of rat peritoneal exudate cells and determined the amino acid sequence of various fragments of that protein. Based on those protein sequences, we then synthesized several antisense oligonucleotide DNA probes corresponding to those regions of purified rat protein which had minimal nucleotide degeneracy. We then used these probes to screen a human cDNA library comprising *E.coli* cells containing human macrophage cDNA sequences inserted into a phage cloning vector.

Figure 4:
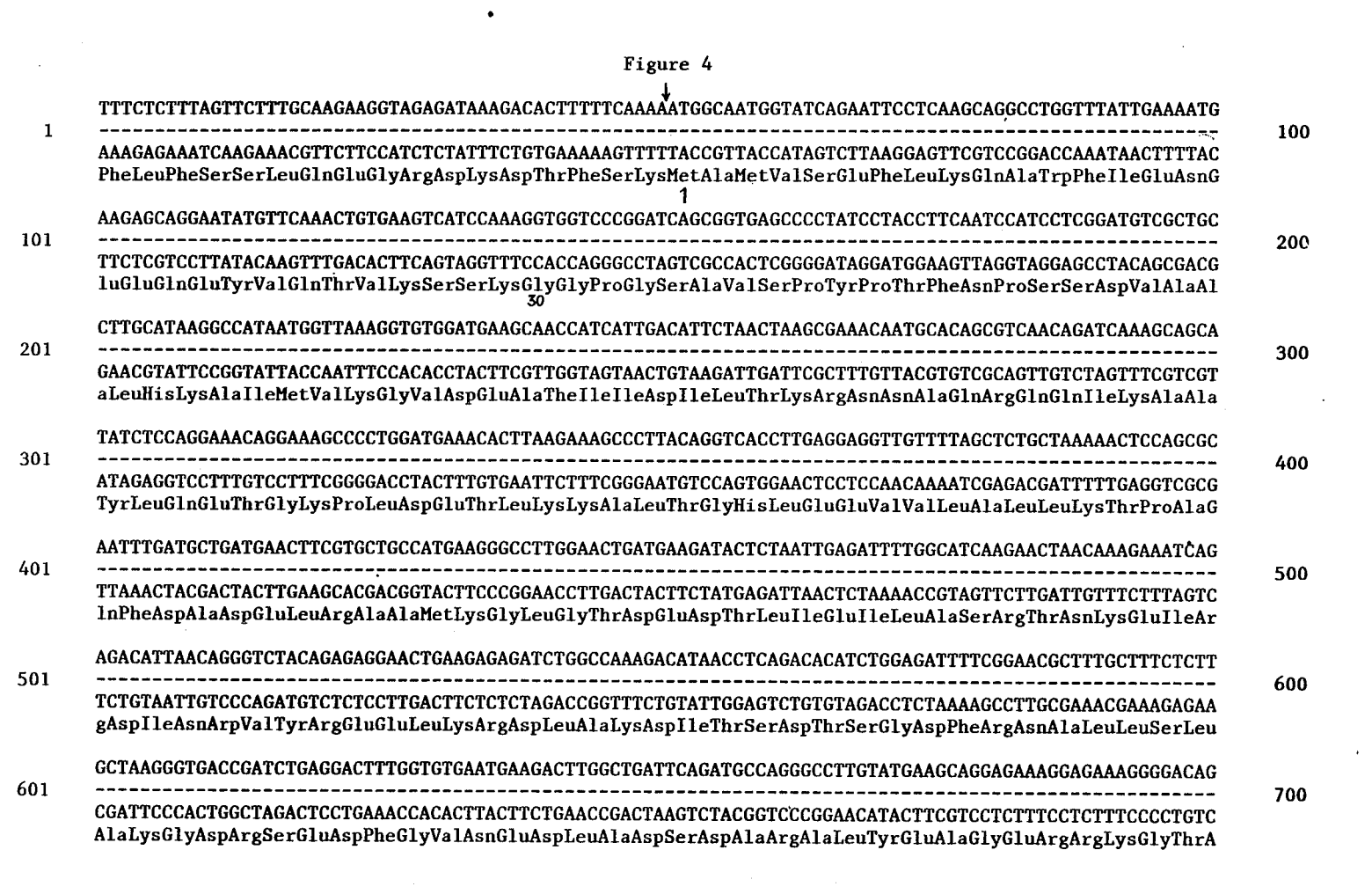

For screening, we hybridized the oligonucleotide probes to the human cDNA library utilizing a plaque hybridization screening assay and we selected clones hybridizing to a number of our probes. After isolating and subcloning the selected human cDNA inserts into plasmids, we determined their nucleotide sequences and compared them to our amino acid sequences from peptides of purified rat lipocortin. As a result of this comparison, we found that the nucleotide sequences of all clones isolated coded for amino acid sequences that had a marked homology to the amino acid sequences of our purified rat lipocortin. (Compare FIGS. 1 and 2 with FIG. 4.) We confirmed that at least one of the clones isolated contained the full length sequence encoding human lipocortin.

The cDNA sequences of this invention can be operatively linked to expression control sequences and used in various mammalian or other eukaryotic or prokaryotic host cells to produce the human lipocortinlike polypeptides coded for by them. For example, we have constructed high level expression vectors for the production of a 37 Kd human lipocortin.

In addition, the cDNA sequences of this invention are useful as probes to screen human cDNA libraries for other sequences coding for lipocortinlike polypeptides. The cDNA sequences of this invention are also useful as probes to screen human genomic DNA libraries to select human genomic DNA sequences coding for lipocortin-like polypeptides. These genomic sequences, like the above cDNA sequences of this invention, are then useful to produce the lipocortinlike polypeptides coded for by them. The genomic sequences are particularly useful in transforming mammalian cells to produce human lipocortin-like polypeptides.

According to a second embodiment of the invention, we isolated from human placenta a human lipocortin-like polypeptide which shows structural similarity, i.e., amino acid homology, to the 37 Kd recombinant lipocortin of this invention. This protein also displays phospholipase $A_2$ inhibitory activity. We have designated the protein, N-lipocortin. Lipocortin and N-lipocortin are discrete proteins that have been defined chemically by tryptic mapping. We determined the amino acid sequences of various fragments of N-lipocortin and based on these sequences, we synthesized antisense oligonucleotide DNA probes. We used these probes to screen a human cDNA library comprising *E.coli* cells containing human placenta cDNA sequences inserted into a phage cloning vector. We isolated several clones which hybridized to the probes. After introducing the cDNA insert of one of these clones into a plasmid, we determined the nucleotide sequence of the cDNA insert. It codes for a portion of N-lipocortin.

This cDNA sequence is useful as a probe to screen human cDNA libraries for other sequences coding for N-lipocortin-like polypeptides. For example, this cDNA insert can be used to screen the human placenta cDNA library of this invention for the full length sequence encoding N-lipocortin. Alternatively, the oligonucleotide probes that were used to obtain the partial N-lipocortin cDNA sequence of this invention are useful as probes to rescreen the placenta library for the full length sequence encoding N-lipocortin. In addition, the N-lipocortin cDNA sequences obtained or the probes described herein may be used to isolate other portions of the N-lipocortin gene and the full length gene reconstructed by standard techniques in the art. Finally, the probes or cDNA sequences may be used as primers to synthesize full length coding sequences.

The N-lipocortin cDNA sequences of this invention are also useful as probes to screen human genomic DNA libraries to select human genomic DNA sequences coding for N-lipocortin-like polypeptides. These genomic sequences, like the N-lipocortin cDNA sequences, are then useful to produce N-lipocortinlike polypeptides in hosts transformed with those sequences.

Another embodiment of the present invention relates to the production of biologically active human lipocortin-like polypeptide fragments which allow better characterization of the active site of the lipocortin protein and the design of molecules having optimal therapeutic value. Accordingly, we have generated such fragments by treatment of the lipocortin-like polypeptides of this invention with various proteases. We have also generated such biologically active fragments by recombinant DNA techniques.

The human lipocortin-like polypeptides produced by the methods of this invention are useful as anti-inflammatory agents and in anti-inflammatory methods and therapies. For example, such compositions may comprise an amount of a lipocortin-like polypeptide of this invention which is pharmaceutically effective to reduce inflammation and a pharmaceutically acceptable carrier. Such therapies generally comprise a method of treating patients in a pharmaceutically acceptable manner with those compositions.

METHODS AND MATERIALS

A wide variety of host/cloning vehicle combinations may be employed in cloning or expressing the human lipocortin-like polypeptide DNA sequences prepared in accordance with this invention. For example, useful cloning or expression vehicles may consist of segments of chromosomal, non-chromosomal and synthetic DNA sequences, such as various known derivatives of SV40 and known bacterial plasmids, e.g., plasmids from *E.coli* including colE1, pCR1, pBR322, pMB9 and their derivatives; wider host range plasmids, e.g., RP4, phage DNAs, e.g., the numerous derivatives of phage λ, e.g., NM 989; and other DNA phages, e.g., M13 and filamentous single-stranded DNA phages and vectors derived from combinations of plasmids and phage DNAs such as plasmids which have been modified to employ phage DNA or other expression control sequences or yeast plasmids such as the 2μ plasmid or derivatives thereof.

Within each specific cloning or expression vehicle, various sites may be selected for insertion of the human lipocortin-like polypeptide DNA sequences of this invention. These sites are usually designated by the restriction endonuclease which cuts them and are well recognized by those of skill in the art. Various methods for inserting DNA sequences into these sites to form recombinant DNA molecules are also well known. These include, for example, dG-dC or dA-dT tailing, direct ligation, synthetic linkers, exonuclease and polymerase-linked repair reactions followed by ligation, or extension of the DNA strand with DNA polymerase and an appropriate single-stranded template followed by ligation. It is, of course, to be understood that a cloning or expression vehicle useful in this invention need not have a restriction endonuclease site for insertion of the chosen DNA fragment. Instead, the vehicle could be joined to the fragment by alternative means.

Various expression control sequences may also be chosen to effect the expression of the DNA sequences of this invention. These expression control sequences include, for example, the lac system, the β-lactamase system, the trp system, the tac system, the trc system, the major operator and promoter regions of phage λ, the control regions of fd coat protein, the promoter for 3-phosphoglycerate kinase or other glycolytic enzymes, the promoters of acid phosphatase, e.g., Pho5, the promoters of the yeast α-mating factors, promoters for mammalian cells such as the SV40 early promoter, adenovirus late promoter and metallothionine promoter, and other sequences known to control the expression of genes of prokaryotic or eukaryotic cells or their viruses and various combinations thereof. In mammalian cells, it is additionally possible to amplify the expression units by linking the gene to that for dihydrofolate reductase and applying a selection to host Chinese hamster ovary cells.

For expression of the DNA sequences of this invention, these DNA sequences are operatively-linked to one or more of the above-described expression control sequences in the expression vector. Such operative linking, which may be effected before or after the chosen human lipocortin DNA sequence is inserted into a cloning vehicle, enables the expression control sequences to control and promote the expression of the DNA sequence.

The vector or expression vehicle and, in particular, the sites chosen therein for insertion of the selected DNA fragment and the expression control sequence employed in this invention, are determined by a variety of factors, e.g., number of sites susceptible to a particular restriction enzyme, size of the protein to be expressed, expression characteristics such as the location of start and stop codons relative to the vector sequences, and other factors recognized by those of skill in the art. The choice of a vector, expression control sequence, and insertion site for a particular lipocortin sequence is determined by a balance of these factors, not all selections being equally effective for a given case.

It should also be understood that the DNA sequences coding for the lipocortin-like polypeptides of this invention which are inserted at the selected site of a cloning or expression vehicle may include nucleotides which are not part of the actual gene coding for the desired lipocortin or may include only a fragment of the entire gene for that protein. It is only required that whatever DNA sequence is employed, a transformed host will produce a lipocortin-like polypeptide. For example, the lipocortin-related DNA sequences of this invention may be fused in the same reading frame in an expression vector of this invention to at least a portion of a DNA sequence coding for at least one eukaryotic or prokaryotic carrier protein or a DNA sequence coding for at least one eukaryotic or prokaryotic signal sequence, or combinations thereof. Such constructions may aid in expression of the desired lipocortin-related DNA sequence, improve purification or permit secretion, and preferably maturation, of the lipocortin-like polypeptide from the host cell. The lipocortin-related DNA sequence may alternatively include an ATG start codon, alone or together with other codons, fused directly to the sequence encoding the first amino acid of a mature native lipocortinlike polypeptide. Such constructions enable the production of, for example, a methionyl or other peptidyl-lipocortin-like polypeptide that is part of this invention. This N-terminal methionine or peptide may then be cleaved intra- or extra-cellularly by a variety of known processes or the polypeptide used together with the methionine attached to the peptide in the anti-inflammatory compositions and methods of this invention.

The cloning vehicle or expression vector containing the lipocortin-like polypeptide coding sequences of this invention is employed in accordance with this invention to transform an appropriate host so as to permit that host to express the lipocortin-like polypeptide for which the DNA sequence codes.

Useful cloning or expression hosts include strains of *E. coli*, such as *E.coli* W3110I$^Q$, *E.coli* JA221, *E.coli* C600, *E.coli* ED8767, *E.coli* DH1, *E.coli* LE392, *E.coli* HB101, *E.coli* X1776, *E.coli* X2282, *E.coli* MRCI, and strains of Pseudomonas, Bacillus, and Streptomyces, yeasts and other fungi, animal hosts, such as CHO cells or mouse cells, other animal (including human) hosts, plant cells in culture or other hosts.

The selection of an appropriate host is also controlled by a number of factors recognized by the art. These include, for example, compatibility with the chosen vector, toxicity of proteins encoded by the hybrid plasmid, susceptibility of the desired protein to proteolytic degradation by host cell enzymes, contamination or binding of the protein to be expressed by host cell proteins difficult to remove during purification, ease of recovery of the desired protein, expression characteristics, biosafety and cost. A balance of these factors must be struck with the understanding that not all host vector combinations may be equally effective for either the cloning or expression of a particular recombinant DNA molecule.

It should be understood that the human lipocortin-like polypeptides (prepared in accordance with this invention in those hosts) may include polypeptides in the form of fused proteins (e.g., linked to a prokaryotic, eukaryotic or combination N-terminal segment to direct excretion, improve stability, improve purification or improve possible cleavage of the N-terminal segment), in the form of a precursor of lipocortin-like polypeptides (e.g., starting with all or parts of a lipocortin-like polypeptide signal sequence or other eukaryotic or prokaryotic signal sequences), in the form of a mature lipocortin-like polypeptide, or in the form of a met-lipocortin-like polypeptide.

One particularly useful form of a polypeptide in accordance with this invention, or at least a precursor thereof, is a mature lipocortin-like polypeptide with an easily cleaved amino acid or series of amino acids attached to the amino terminus. Such construction allows synthesis of the protein in an appropriate host, where a start signal that may not be present in the mature lipocortin is needed, and then cleavage in vivo or in vitro of the extra amino acids to produce mature lipocortin-like polypeptides. Such methods exist in the art. See, e.g., U.S. Pat. Nos. 4,332,892, 4,338,397, and 4,425,437. The polypeptides may also be glycosylated, like some native lipocortins, unglycosylated, or have a glycosylation pattern different than that of native lipocortins. Such glycosylation will result from the host cell or post-expression treatment chosen for the particular lipocortin.

The polypeptides of this invention also include biologically active polypeptide fragments derived from lipocortin-like polypeptides by treatment with proteases or by expression of a fragment of the DNA sequence which codes for a lipocortin-like polypeptide. The polypeptides of the invention also include lipocortin-like polypeptides that are coded for on expression by DNA sequences characterized by different codons for some or all of the codons of the present DNA sequences. These substituted codons may code for amino acids identical to those coded for by the codons replaced but result in higher yield of the polypeptide. Alternatively, the replacement of one or a combination of codons leading to amino acid replacement or to a longer or shorter lipocortin-like polypeptide may alter its properties in a useful way (e.g., increase the stability, increase the solubility or increase the therapeutic activity).

In order that this invention may be better understood, the following examples are set forth. These examples are for purposes of illustration only and are not to be construed as limiting the scope of the invention in any manner.

EXAMPLES

A. PURIFICATION OF A RAT PHOSPHOLIPASE $A_2$ INHIBITOR PROTEIN

We injected male Wistar rats (200–250 kg) subcutaneously with 0.1 ml of the glucocorticoid, dexamethasone phosphate (1.25 mg/kg rat) in 0.9% NaCl to induce production of phospholipase $A_2$ inhibitor protein. We then sacrificed the rats one hour after injection by intracardiac injection with Euthasate and washed the peritoneal cavities with 10 ml of phosphate buffered saline (50 mM $KH_2PO_4$, pH 7.3, 150 mM NaCl containing 2 U/ml heparin and 50 $\mu$M phenylmethylsulfonylfluoride). After we cleared the lavages of cells and other particulate matter by centrifugation in an International centrifuge at top speed for 30 min, we assayed the combined supernatants for lipocortin by measuring the inhibition of release of labeled oleic acid from autoclaved *E.coli* membranes in the presence of the supernatant and porcine pancreatic phospholipase $A_2$.

We performed this in vitro assay as follows: We mixed 200 $\mu$l samples from the peritoneal exudate supernatant in 1.5 ml Eppendorf tubes with 50 $\mu$l of 0.7M Tris-HCl (pH 8.0), 60 mM $CaCl_2$ buffer on ice. We then added 50 $\mu$l of diluted porcine pancreatic phospholipase $A_2$ (Catalogue no. P9139, Sigma Chemicals) and mixed and incubated the solutions on ice for 1 h. Dilutions of the phospholipase $A_2$ suspension into buffer (70 mM Tris-HCl (pH 8.0), 6 mM $CaCl_2$) containing 2.5 mg/ml bovine serum albumin (BSA) were such that the final concentrations of phospholipase and BSA were 100 ng/50 $\mu$l and 125 $\mu$g/50 $\mu$l, respectively. We then added 25 $\mu$l of autoclaved $^3$H-oleic acid-labeled *E.coli* as substrate and incubated the mixtures at 6° C. for 8 min (both the temperature and length of incubation must be determined for each batch of *E.coli* utilized).

We prepared the substrate $^3$H-oleic acid-labeled *E.coli* as follows: We grew an overnight culture of *E.coli* in tryptone medium (1% bactotryptone, 0.5% NaCl) diluted it 1:20 with fresh broth and monitored cell growth with a Klett meter. At a reading of 40 (i.e., when cells were growing well), we added a 1:100 dilution of Brij 35 (polyoxyethylene-23-ether, Sigma Chemicals, 10% solution in water) and a 1:200 dilution of $^3$H-oleic acid (9,10-$^3$H-[N]oleic acid, New England Nuclear) at 10 mCi/ml. After 5 h, when cell growth leveled off, we autoclaved the suspension for 20 min at 120° C. and stored the flask overnight at 4° C. We then pelleted the bacteria by centrifugation for 30 min at 16,000 rpm in an SS34 rotor at 4° C. and combined the loose pellets into a single tube. We washed the bacteria four times, or until counts in the supernatant were low, with suspension buffer (0.7M Tris-HCl (pH 8.0), 10 mM $CaCl_2$) plus 0.1% BSA. We stored the bacteria at 4° C. in suspension buffer containing 0.2% sodium azide. Typically, we prepared a 400 ml culture labeled with 20 mCi of $^3$H-oleic acid. This yielded about $7 \times 10^8$ cpm or about 10% of the input counts in labeled bacteria. For each point in an assay, we used 100,000 cpm, which was added in a volume of 25 $\mu$l. Immediately prior to use, we washed our aliquots first in 200 mM Tris-HCl (pH 8.0), 12 mM EDTA (left on ice 30 min) and then in 25 mM Tris-HCl (pH 8.0).

After the brief incubation of substrate (autoclaved labeled *E.coli*) with inhibitor plus phospholipase $A_2$, the reaction was stopped immediately by adding 100 $\mu$l of 2N HCl to each tube followed by the addition of 100 $\mu$l of 20 mg/ml delipidated BSA (99% albumin, Sigma Chemicals). Tubes were vortexed and incubated on ice for 30 min. The latter step was crucial for extracting the lipase digestion products from the particulate membranes.

We then pelleted the *E.coli* in an Eppendorf centrifuge for 5 min at 10,000 g and counted 250 $\mu$l of each supernatant in 4 ml of a scintillation cocktail compatible with aqueous solutions. In this assay, we tested each sample in duplicate using an internal control in which the sample plus *E.coli* substrate was incubated both in the presence and absence of added phospholipase. This in vitro assay demonstrated that our peritoneal exudates contained phospholipase inhibitory activity.

To purify the lipocortin from the abovedescribed peritoneal exudate supernatant, we first added additional protease inhibitors to the supernatant. These typically included aprotinin (20 $\mu$g/ml), soybean trypsin inhibitor (20 $\mu$g/ml) and EGTA (ethyleneglycol-bis-(aminoethyl ether) N,N'-tetraacetic acid) (0.5 mM). We incubated the exudate at 37° C. for 1 h in the presence of 0.1 U/ml calf intestinal alkaline phosphatase and concentrated it two-fold by ultrafiltration to a final protein concentration of 5 mg/ml using an Amicon apparatus (PM10 membrane). We next dialyzed the supernatant overnight at 4° C. against 40 volumes of 20 mM Tris-HCl (pH 8.1) and subjected it to DE52 ion exchange column chromatography (Whatman Ltd., column dimensions: 1 cm dia. $\times$ 17 cm). Prior to use, we had equilibrated the DE52 resin with 25 mM Tris-HCl (pH 8.1). We collected the flow-through fractions and concentrated them an additional 25-fold by Amicon ultrafiltration (PM10 membrane). We then subjected the concentrate to a gel filtration column (P150 resin) in 25 mM Tris-HCl (column dimensions 2.5 cm dia. $\times$ 40 cm) and monitored the column fractions for protein using absorbance at 280 nm and using the phospholipase inhibitory activity assay described above. We detected peak activity at 35–40,000 molecular weight.

We lyophilized these high activity fractions, dialyzed them against 25 mM Tris-HCl (pH 6.8) containing 0.2% SDS and analyzed them using a preparative SDS-polyacrylamide gel (main gel: 15% acrylamide, 0.08% methylene bisacrylamide; stacking gel: 7.6% acrylamide, 0.21% methylene bisacrylamide). The gel analysis yielded four major protein bands. According to a modification of the Western blotting technique [H. Towbin et al., "Electrophoretic Transfer Of Proteins From Polyacrylamide Gels To Nitrocellulose Sheets", Proc. Natl. Acad. Sci. USA, 76. pp. 4350–54 (1979)] using a horse radish peroxidase antibody conjugate to visualize the immunoreactive species, we found that only one of the four major bands cross reacted with a neutralizing antibody which we prepared against a snake venom lipocortin. Accordingly, we excised this region of the gel, electroeluted and precipitated the contained protein from it with 20% trichloroacetic acid and pelleted the protein by centrifugation for 20 min at 10,000 g. After washing the pellets twice with 5 ml of $-20°$ C. acetone, each washing being followed by a centrifugation step, we dried the pellets under vacuum.

We then digested the protein either with cyanogen bromide or with trypsin. When utilizing cyanogen bromide digestion, we digested the pellets containing approximately 100 μg protein with 200 mg/ml of cyanogen bromide in the dark for 16 h at 25° C. in 0.5 ml of 70% formic acid. We then diluted the reaction mixture 15-fold with water and lyophilized it. When utilizing tryptic digestion, we first resuspended the pellets in 0.1M $NH_4HCO_3$ plus 0.1 mM $CaCl_2$, carboxymethylated the mixture with iodoacetic acid and then incubated it with trypsin for 24 h at 37° C. During this incubation, we added trypsin three times to a final concentration of 1.5% of total protein at time zero, 2.5% after 4 h and 3.5% after 19 h.

We resolved the cleavage fragments from these digestions by high pressure liquid chromatography using a C8 column (Brownlee RP-3) for the cyanogen bromide digestion products and using a C18 column (Spectraphysics) for the tryptic digestion products, utilizing in both cases a gradient of acetonitrile from 0–75% in 0.1% trifluoroacetic acid to elute bound fragments. We then subjected the peak fractions to sequence analysis using a gas phase sequencer (Applied Biosystems 470A). PTH-amino acids were analyzed by high pressure liquid chromatography on a 5 μm cyanocolumn (Hypersil), using a gradient of acetonitrile:methanol (4:1) from 15–55% in 0.02M sodium acetate (pH 5.7).

FIG. 1 shows the amino acid sequences of the fragments produced by cyanogen bromide digestion of our purified rat lipocortin. Of six major peaks, only three yielded unique sequences (CNBr 1, 2 and 3). These sequences are shown at the bottom of FIG. 1. Of the remaining peaks, two (CNBr 5 and 6) contained mixtures of fragments and thus could not be sequenced, and peak 4 was a column artifact from which no protein was detected.

FIG. 2 shows the amino acid sequences of fragments from tryptic digestion. Although tryptic digestion produced over forty peaks, the amino acid sequences of only nine fractions are shown in FIG. 2. In instances where peaks contained more than one peptide, the appropriate fractions were subjected to a second chromatography step. T22a and T22b are sequences derived from the two components of peak 22 which were resolved when peak 22 was rechromatographed on the same column but at a neutral pH.

B. SYNTHESIS OF OLIGONUCLEOTIDE DNA PROBES FOR LIPOCORTIN PROTEIN SEQUENCES

Having determined the amino acid sequences of various regions of a rat lipocortin (see FIGS. 1 and 2), we chemically synthesized four pools of antisense oligonucleotide DNA probes that coded for some of those protein sequences (see FIG. 3). We decided to synthesize the four pools shown in FIG. 3 because they corresponded to regions of the rat lipocortin that have minimal nucleic acid degeneracy. For each amino acid sequence, we synthesized mixtures of probes complementary to all possible codons. Furthermore, we synthesized the probes such that they were complementary to the DNA sequences which code for the amino acid sequence, i.e., the probes were antisense, to enable the probes to recognize the corresponding sequences in mRNA as well as in DNA. The amino acid sequences of the four selected regions of the rat lipocortin and all the possible nucleotide codon combinations that encode them are shown in FIG. 3. Coding degeneracies are indicated as follows: N=C, T, A, or G; R=A or G; Y=C or T; and H=A, C, or T.

Two pools of the probes, derived from sequences in the tryptic fragments T22a and T24 of FIG. 2, are 20-mers with 48 and 256 fold degeneracies, respectively. The other two probe pools are 17-mers with 64 and 128 fold degeneracies. To reduce further the degeneracies in the probes, we also prepared each pool in subpools, e.g., we prepared the 48 fold degenerate 20-mer of T22a in three subpools of 16 and synthesized the other probes in four subpools. The probes in each pool were end-labeled with $^{32}P$ using $[\gamma]$-$^{32}P$-ATP and T4 polynucleotide kinase.

To test if our synthetic probes actually recognized human sequences, we hybridized the four subpools of T24 to GeneScreen filters containing poly (A)$^+$ mRNA from the human macrophage cell line U937, which had been induced with $10^{-7}$M PMA[4β-phorbol 12βmyristate 13α-acetate] and $10^{-5}$ dexamethasone, utilizing the Northern blotting technique [H. Lehrach et al., Biochemistry, 10, pp. 4743–51 (1977)]. Subpools 2 and 3 of T24 hybridized to the mRNA and were detected as an 1800 base pair band upon autoradiography.

C. CONSTRUCTION AND SCREENING OF A HUMAN cDNA LIBRARY

We constructed a human cDNA library from poly (A)$^+$ mRNA isolated from human macrophage cell line U937. The cDNA sequences were inserted into λgt10 and amplified in E.coli C600 hfl cells.

1. EXTRACTION OF RNA FROM HUMAN U937 CELLS

We induced human macrophage U937 cells in culture with dexamethasone ($10^{-5}$M) and phorbol ester ($10^{-7}$M) and resuspended pellets containing $1.2 \times 10^9$ cells in 48 ml lysis buffer (0.2M Tris-HCl (pH 8.0), 0.1M LiCl, 25 mM EDTA, 1% SDS) plus 5 mM vanadyl complex (Bethesda Research Labs) by vortexing. We lysed the cells by addition of 24 ml phenol and vortexed for 5 min. We added 24 ml chloroform to the lysis mixture which was then shaken for 10 min. We separated the organic and aqueous phases by centrifugation in a clinical centrifuge at room temperature for 10 min. We reextracted the aqueous phase two times with phenol:chloroform (1:1), then two times with chloroform only. We next ethanol-precipitated the nucleic acids in 0.3M sodium acetate at $-20°$ C. overnight and pelleted the nucleic acid at 14 k rpm in a Sorvall RC2B centrifuge (SS34 rotor) at 4° C. for 20 min. We resuspended the pellets in 5 ml of 0.3M sodium acetate buffer, and ethanol-precipitated the nucleic acid again as described above. We resuspended the final pellet in 300 μl $H_2O$ and stored it at −20° C. This RNA preparation was enriched for poly(A)+ RNA by passage over an oligo(dT)-cellulose column (PL Biochem).

2. CONSTRUCTION OF A U937 cDNA-λgt10 LIBRARY cDNA Synthesis

We synthesized cDNA from 20 μg poly (A)+ mRNA isolated as described above. We diluted the poly (A) mRNA to 500 μg/ml in H₂O, heated it to 65° C. for 3 min, quick cooled it in a dry ice-propanol bath and then thawed it. The RNA was then added to a reaction mixture composed of 0.1M Tris-HCl (pH 8.3) at 42° C., 0.01M MgCl$_2$, 0.01M DTT, 1 mM dCTP, 1 mM dGTP, 1 mM dTTP, 0.5 mM dATP and 100 μCi α-$^{32}$P-ATP (3000 Ci/mmole, Amersham or New England Nuclear), 20 μg oligo (dT)$_{12-18}$ (PL Biochem), 0.03M β-mercaptoethanol, 5 mM Vanadyl Ribonucleoside Complex (Bethesda Research Labs), 169 U AMV Reverse Transcriptase (Seikagaku America). Final volume of the reaction mixture was 200 μl. We incubated this mixture for 2 min at room temperature and 6 h at 44° C. We terminated the reaction by addition of 1/10 vol 0.5M Na$_2$EDTA (pH 8.0).

We adjusted the reaction mixture to 0.15M NaOH and incubated the mixture at 37° C. for 12 h followed by neutralization with 1/10 vol 1M Tris-HCl (pH 8.0) and HCl. This was extracted with phenol:chloroform saturated TE buffer (10 mM Tris-HCl (pH 7.0) and 1 mM Na$_2$EDTA). The aqueous phase was chromatographed through a 5 ml sterile plastic pipet containing a 7×29 cm bed of Sephadex G150 in 0.01M (pH 7.4), 0.4M NaCl, 0.01M Na$_2$EDTA, 0.05% SDS. We pooled the front peak minus tail and precipitated the cDNA with 2.5 vol 95% ethanol at −20° C. This reaction yielded 1 μg of single-stranded cDNA.

Double Strand Synthesis

We resuspended the single-stranded cDNA in 200 μl (final vol) 0.1M Hepes (pH 6.9), 0.01M MgCl$_2$, 0.0025M DTT, 0.07M KCl, 1 mM dXTPs and 75 U Klenow fragment DNA polymerase 1 (Boehringer-Mannheim) and incubated the reaction mixture at 14° C. for 21 h. Reaction was terminated by addition of Na$_2$EDTA (pH 8.0) to 0.0125M, extracted with phenol:chloroform, as in the first cDNA step, and the aqueous phase was chromatographed on a G150 column in 0.01M Tris-HCl (pH 7.4), 0.1M NaCl, 0.01M Na$_2$EDTA, 0.05% SDS. We again pooled the radioactive peak minus the tail and ethanol-precipitated the DNA.

We then incubated the DNA obtained with 42 U reverse transcriptase in 50 μl 1 0.1M Tris-HCl (pH 8.3), 0.01M MgCl$_2$, 0.01M DTT, 0.1M KCl, 1 mM dXTPS, 0.03M β-mercaptoethanol for 1 h at 37° C. to complete double-strand synthesis. The reaction was terminated and processed as described above.

We cleaved the hairpin loop formed during double strand synthesis as follows: We redissolved the pellet in 50 μl 0.03M sodium acetate (pH 4.5), 0.3M NaCl, 0.003M ZnCl$_2$ and treated it with 100 U S$_1$ nuclease (Sigma) for 30 min at room temperature. Reaction was terminated by addition of EDTA and processed as described above. The yield after S$_1$ treatment was 900 ng dsDNA.

To assure blunt ends following S$_1$ nuclease digestion, we treated the DNA with Klenow in 0.01M Tris-HCl (pH 7.4), 0.01M MgCl$_2$ 1 mM DTT, 0.05M NaCl, 80 μM dXTP and 12.5 U Klenow in 60 μl for 90 min at 14° C. extracted with 50:50 phenol:chloroform, and chromatographed the DNA on a G50 spin column (1 ml syringe) in 0.01M Tris-HCl (pH 7.4), 0.1M NaCl, 0.01M EDTA, 0.05% SDS.

We next methylated the dsDNA by treating the DNA with EcoRI methylase in 30 μl final vol 0.1M Tris-HCl (pH 8.0), 0.01M Na$_2$EDTA, 24 μg BSA, 0.005M DTT, 30 μM S-adenosylmethionine and 5 U EcoRI Methylase for 20 min at 37° C. The reaction was heated to 70° C. for 10 min, cooled, extracted with 50:50 phenol:chloroform and chromatographed on a G50 spin column as described above.

We ligated the 900 ng cDNA to phosphorylated EcoRI linkers (New England Biolabs) using the following conditions: 0.05M Tris-HCl (pH 7.8), 0.01M MgCl$_2$, 0.02M DTT, 1 mM ATP, 50 μg/ml BSA, 0.5 μg linker, 300 U T4 DNA ligase in 7.5 μl final volume for 32 h at 14° C.

We adjusted the reaction to 0.1M Tris-HCl (pH 7.5), 0.05M NaCl, 5 mM MgCl$_2$, 100 μg/ml BSA, 125 U EcoRI (New England Biolabs), incubated the mixture for 2 h at 37° C., extracted with 50:50 phenol:chloroform and chromatographed the DNA on a G50 spin column as described earlier.

We redissolved cDNA in 100 μl 0.01M Tris-HCl (pH 7.5), 0.1M NaCl, 1 mM EDTA and chromatographed it on a 1×50 cm Biogel A$_{50}$ (BIORAD) column which had been extensively washed in the same buffer (to remove ligation inhibitors). Aliquots of fractions were run on a 1% agarose gel in TBE buffer (0.089M Tris-HCl, 0.089M boric acid and 2.5 mM Na$_2$EDTA), dried and exposed at −70° C. overnight. We pooled all fractions that were larger than 500 base pairs and ethanol-precipitated the DNA for cloning into an EcoRI-cut λgt10 cloning vector. The size fractionation column yielded 126 ng of cDNA, average size approximately 1500 bp.

Library Construction

We incubated 5 μg EcoRI-cut λgt10 with 20 ng cDNA and T4 DNA ligase buffer at 42° C. for 15 min to anneal cos sites, followed by centrifugation for 5 sec in an Eppendorf centrifuge and addition of ATP to 1 mM and 2400 U T4 DNA ligase (New England Biolabs) in a final vol of 50 μl. [See Huynh, Young and Davis, "Constructing And Screening cDNA Libraries in λgt10 And λgt11", in *DNA Cloning A Practical Approach* (D. Glover, ed.), IRL Press (Oxford 1984).] The ligation was incubated at 14° C. overnight. We packaged the λgt10 cDNA ligation mixture into phage particles using an Amersham packaging mix [Amersham packaging protocol] and diluted with 0.5 ml SM buffer (100 mM NaCl, 10 mM MgSO$_4$, 50 mM Tris-HCl (pH 7.5) and 0.01% gelatin).

We next infected *E.coli* C600 hfl cells with these phage particles to form a cDNA library of 1×10$^7$ independent recombinants [see T. Maniatis, et al., *Molecular Cloning*, p. 235 (Cold Spring Harbor 1982)].

For plating and amplification of the library, 1 ml of cells plus 250 μl packaging mix was incubated at room temperature for 15 min, diluted to 50 ml in LB plus MgSO$_4$ top agarose at 50° C. and plated on LB Mg Nunc plates. This represented a plaque density of 2×10$^5$ plate. The plates were incubated at 37° C. for approximately 8 h until plaques were nearly touching.

We flooded the plates with 50 ml of cold SM buffer (0.01M Tris-HCl (pH 7.5), 0.01M MgCl$_2$, 0.1 mM Na₂EDTA) and eluted on a gyro-rotary shaker overnight at 4° C. We pooled the eluants into 250 ml bottles and spun at 6 k for 10 min in a Sorvall GSA rotor. We treated the supernatants with an equal volume of cold 20% PEG 4000-2M NaCl in ice for 3 h and pelleted the phages by centrifugation at 4 k for 30 min in an H4000 rotor in an RC-3B Sorvall centrifuge. The phage pellets were thoroughly drained, resuspended in 60 ml SM, and spun at 10,000 rpm in a SS34 rotor to remove debris. The supernatants were adjusted to 3.5M CsCl by addition of 7 g CsCl to 10 ml supernatant. We obtained phage bands by centrifugation in a 70.1 Beckman rotor at 50,000 rpm for 18 h at 15° C. We pooled the phage bands and stored them at 4° C. for library stock. The titer obtained was $2.2 \times 10^{13}$ PFU/ml.

Screening Of The Library

We screened the library with our labeled oligonucleotide probes, pools 2 and 3, for lipocortin sequences using the plaque hydridization screening technique of Woo [S. L. C. Woo, "A Sensitive And Rapid Method For Recombinant Phage Screening", in *Methods In Enzymology*, 68, pp. 389-96 (Academic Press 1979)].

An overnight culture of C600 hfl cells in L broth and 0.2% maltose was pelleted and resuspended in an equal volume of SM buffer. We pre-adsorbed 0.9 ml of cells with $2 \times 10^5$ phage particles at room temperature for 15 min. We diluted the suspension to 50 ml in LB plus 10 mM MgSO₄ and 0.7% agarose at 55° C. and plated it on LB Mg Nunc plates. We screened 10 such plates. We incubated the plates at 37° C. for approximately 8 h until plaques were nearly touching. We then chilled the plates at 4° C. for 1 h to allow the agarose to harden. We presoaked GeneScreen Plus filters in a 1:10 dilution of the overnight *E.coli* C600 hfl cells for 10 min at room temperature so that a lawn of *E.coli* cells covered each filter. We then transferred the λ phage particles from the plaque library plates to these bacteria-coated filters as follows:

We placed the filters onto the plates containing the recombinant plaques for 5 min, and then lifted and incubated the filters with the phage-containing side up on LB+10 mM MgSO₄ plates at 37° C. for 5 h.

These filters were then lysed by placing them onto a pool of 0.5N NaOH for 5 min, then neutralized on 1M Tris-HCl (pH 7.0), submerged into 1M Tris-HCl (pH 7.0) and scrubbed clean of cell debris.

We prehybridized and hybridized the filters to the oligonucleotide probes 2 and 3 in 0.2% polyvinyl-pyrrolidone (M.W. 40,000), 0.2% ficoll (M.W. 40,000), 0.2% bovine serum albumin, 0.05M Tris-HCl (pH 7.5), 1M sodium chloride, 0.1% sodium pyrophosphate, 1% SDS, 10% dextran sulfate (M.W. 500,000) and denatured salmon sperm DNA ($\geq$100 μg/ml) according to manufacturer's specifications (New England Nuclear) for plaque screen membranes). We detected hybridizing λ-cDNA sequences by autoradiography.

By means of this technique, we picked 20 positive plaques and rescreened at lower density using the same probes.

We isolated the DNA of these clones, digested with EcoRI, and hybridized them with the four pools of rat lipocortin probes using the Southern blot technique [E. M. Southern, "Detection Of Specific Sequences Among DNA Fragments Separated By Gel Electrophoresis", *J. Mol. Biol.*, 98. pp. 503-18 (1975)]. Two of the clones, λ9-111 and λ4-211, contained inserted cDNA which hybridized not only to the T24 probe but to the T22a and T29 probes as well.

We restricted the DNAs of these phages with EcoRI and isolated the cDNA inserts. By restricting Clone 9-111 with EcoRI we obtained a 1400 base pair fragment while restriction of Clone 4-211 gave three EcoRI fragments, 1300, 300 and 75 base pairs in length. We subcloned some of these fragments into plasmid pUC13 to produce recombinant plasmids pL9/20 (9-111), pL4/10 large (4-211, 1300 bp), and pL4/10 small (4-211, 300 bp). We then sequenced these plasmids by the method of Maxam and Gilbert [A. M. Maxam and W. Gilbert, "A New Method For Sequencing DNA", *Proc. Natl. Acad. Sci. USA*, 74, pp. 560-64 (1977)]. This sequencing analysis demonstrated that the clones contained nucleotide sequences which corresponded to the amino acid sequences of the purified rat lipocortin but seemed to be lacking the most 5' sequence.

A 480 base pair EcoRI-BglII fragment of pL9/20 was used as a probe to rescreen the U937-λgt10 library. Seventy-two positives were isolated and partially plaque purified by rescreening at lower density. The DNA of each of these positives was digested with HhaI and analyzed by the Southern blotting technique [E. M. Southern, supra] using a 30 oligonucleotide sequence (lipo 16) as a probe. Lipo 16 corresponds to the sequence starting at base pair 81-111 of the sequence presented in FIG. 4. Fourteen of these clones showed a positive signal and were further analyzed by genomic sequencing [G. Church and W. Gilbert, *Proc. Natl. Acad. Sci. USA*, 81, p. 1991 (1984)] by digesting DNA with MspI and using lipo 16 as probe. Seven clones, λL110, λL106, λL112, λLC, λLH, λN, and λLDD, contained an 81 base pair sequence 5' to the lipo 16 probe sequence.

These clones contain cDNA sequences having an uninterrupted open reading frame that can code for 363 amino acids (see FIG. 4). We believe that the initiating ATG codon for lipocortin may be the ATG located at nucleotides 52-54 of FIG. 4. However, the DNA sequence of our clone, reported in FIG. 4, may be lacking one or more codons coding for amino acids at the N-terminal end of native lipocortin. These potential missing codons may be isolated, if necessary, by one of skill in the art using conventional hybridization conditions from our libraries, or other libraries, of genomic DNA and cDNA using as probes our clones, or more preferably portions of the 5' terminal end of those clones. Full length clones may then be prepared using conventional ligation techniques and our lipocortin coding clones.

We confirmed that clone λLC of FIG. 4 contains the full length gene for lipocortin. To confirm that the ATG at nucleotides 52-54 in the λLC cDNA (FIG. 4) is the first in-frame methionine codon and thus the initiating methionine, we determined the 5' sequence of the lipocortin mRNA by primer extension. A 27 oligonucleotide (lipo 18) homologous to the sequence 10 to 37 of λLC was labelled with $^{32}$P-(γ)-ATP and hybridized to human placental poly (A)+ RNA. Using this oligonucleotide as a primer and AMV reverse transcriptase, we transcribed a 60 base pair fragment of the most 5' end of the lipocortin mRNA. This fragment was gel purified and sequenced by the Maxam and Gilbert sequencing technique (supra). The resulting sequence showed 37 base pairs homologous to sequence 1 to 37 of λLC and 23 additional nucleotides that represented the 5' end of the lipocortin mRNA.

To exclude the possibility that the mRNA was in fact longer than our primer extension indicated, but instead had a strong stop signal for reverse transcriptase which we mistook for the 5' end, we determined the exact size of the mRNA. An oligonucleotide (lipo 17) that is homologous to sequence 94 to 128 of λLC was hybridized to placental poly (A)+ RNA and digested with RNase H. RNase H digests RNA only when in a hybrid with DNA and thus it introduced a defined cleavage in the mRNA at the site where lipo 17 hybridized. This RNA was then separated on a sequencing gel, blotted onto GeneScreen and probed with $^{32}$P-labelled lipo 18. This enabled us to determine the exact size of the 5' end of the lipocortin mRNA, which agreed with the size obtained by primer extension.

The cDNA sequences of this invention can be further utilized to screen human genomic cosmid or phage libraries to isolate human genomic sequences encoding human lipocortin-like polypeptides.*

* For example, an EcoRI fragment of plasmid pL9/20 was used to screen a partial HaeIII-AluI human liver library (R. Lawn et al., "The Isolation And Characterization of Linked δ and β Globin Genes From A Cloned Library of Human DNA", Cell, 15, pp. 1157–74 (1978)), and positive clones were obtained.

These human cDNA and genomic sequences can be used to transform eukaryotic and prokaryotic host cells by techniques well known in the art to produce human lipocortin-like polypeptides in clinically and commercially useful amounts.

It should also be understood that the cDNA sequences of the invention may be contained in larger mRNA species which result from alternate splicing. Such mRNAs may encode a signal sequence for lipocortin in addition to the mature protein.

D. EXPRESSION OF A LIPOCORTIN PROTEIN IN E.COLI

Plasmid pKK233.LIP.1 (which contains a partial sequence of the lipocortin coding region) was constructed by a three part ligation using NcoI-Pst -cut pKK233-2 [E. Amann et al., "Vectors Bearing A Hybrid Trp-Lac Promoter Useful For Regulated Expression Of Cloned Genes In *Escherichia coli*", Gene, 25 pp. 167–78 (1983)] and the BglII-PstI and NciI-BglII fragments from pL9/20 (see FIG. 5). Plasmid pL9/20 contains the DNA sequence of nucleotides 67–1376 of the cDNA insert of λLC shown in FIG. 4 inserted into the EcoRI site of pUC13.

Transformants resulting from this ligation and subsequent transformation into *E.coli* strain HB101 IQ were picked into microtiter wells containing L broth plus ampicillin and grown overnight. The overnight cultures were then replicated onto nitrocellulose filters on L broth agar plus ampicillin plates in quadruplicate and incubated for approximately 4 h at 37° C. The nitrocellulose filters were then transferred to L broth plates containing IPTG (10 μg/ml) and incubated for 0, 30, 60, or 120 min, followed by lysozyme-detergent treatment to lyse the colonies and finally by Western blot analysis with a cross reactive antiserum that was prepared against the rat lipocortin. Transformants were also analyzed by plasmid restriction mapping. All the Western positive colonies contained plasmids carrying the predicted restriction fragments. Preparations of *E.coli* from the positive colonies were also analyzed by SDS polyacrylamide gel electrophoresis. With Western blot analysis of these preparations using the antibody against rat lipocortin, we detected a 31,000 molecular weight truncated protein.

We have also constructed various expression vectors in *E.coli* for the production of the full length human lipocortin. All are perfect constructs starting with the first methionine in the sequence depicted in FIG. 4. We confirmed expression by the procedure described above for the truncated protein, using an antiserum prepared against rat lipocortin.

Figure 6:
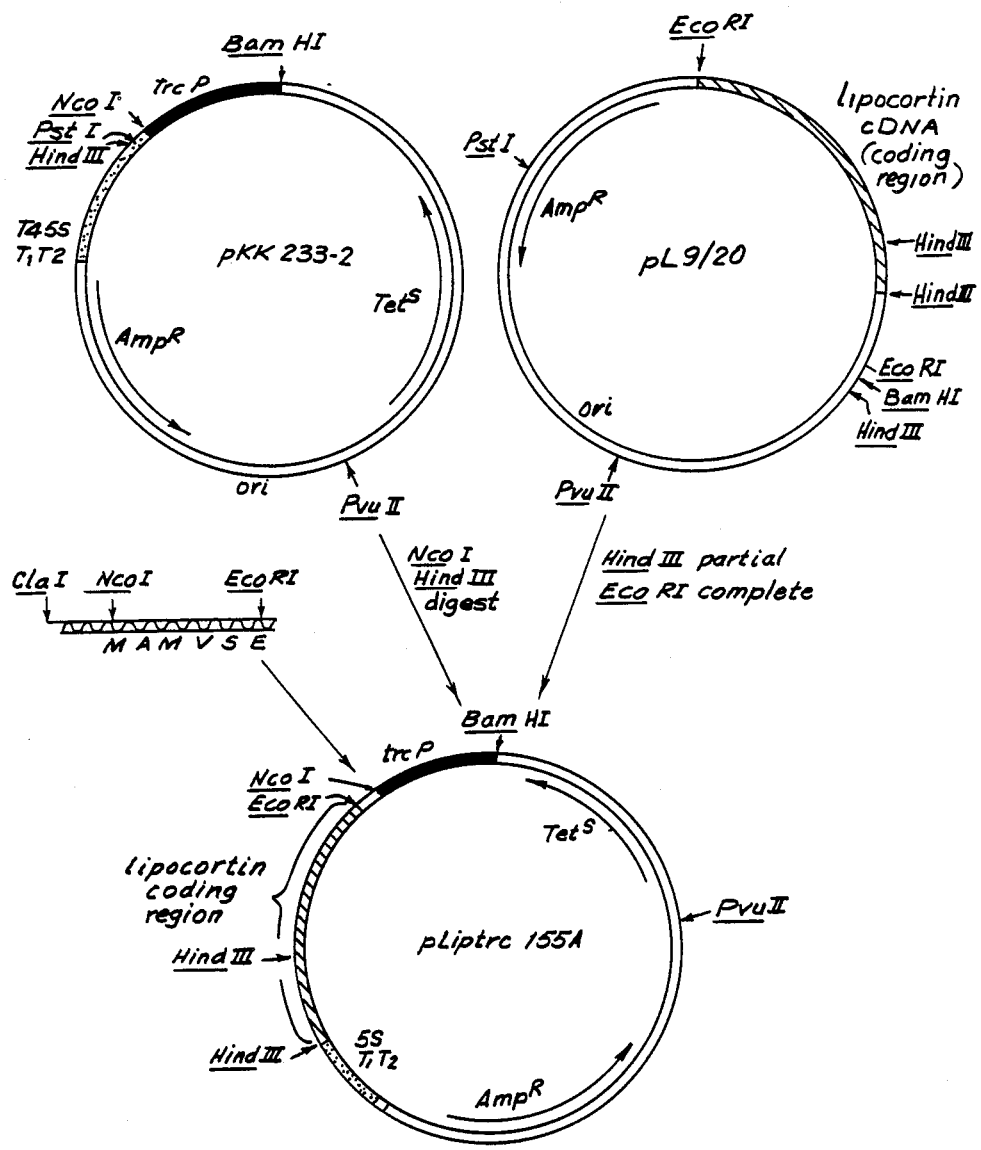
FIG. 6 depicts in schematic outline the construction of plasmid pLiptrc155A used to express in one embodiment the DNA sequences of the invention.

For example, FIG. 6 depicts plasmid pLiptrc155A, a trc expression vector derived from plasmid pKK233-2 [E. Amann et al., supra]. pLiptrc155A has a hybrid promoter which contains the −10 region from lac and the −35 region from trp. It also contains the 5S RNA $T_1T_2$ terminators and the β-lactamase gene which confers ampicillin resistance.

pLiptrc155A was constructed as follows: Plasmid pKK233-2 was restricted with NcoI and HindIII, yielding a linear fragment. Plasmid pL9/20 was partially digested with HindIII and then completely digested with EcoRI and the 1090 fragment was isolated by agarose gel electrophoresis. These two fragments were then completely digested ligated in the presence of a NcoI-EcoRI linker containing the initiation ATG and the sequence coding for five amino acids 5' to the EcoRI site in the human lipocortin cDNA.

The resulting pLiptrc155A expression vector was then used to transform *E.coli* strains JA221 and W3110IQ and expression was induced by growth of the transformed strains for 4 h in LB medium containing 1 mM IPTG and 35 μg/ml ampicillin. SDS polyacrylamide gel analysis of crude lysates of the transformed host cells showed a single new protein band at an apparent molecular weight of 37 Kd. Control extracts from the strains not transformed with pLiptrc155A, or strains transformed with the plasmid but suppressed for production of the protein, did not show this 37 Kd protein. We found, for example, that when the JA221 host was transformed with pLiptrc155A, the 37 Kd protein accounted for as much as 2% of the total protein.

To further verify that we were expressing the human lipocortin, the same lysates were also subjected to Western blot analysis using antibody raised against the rat lipocortin. Only the 37 Kd protein was immunoreactive with the antibody against the rat protein. We have also shown by Western blot analysis that the natural human lipocortin from U937 cells (detected by its immunoreactivity with the anti-rat protein antibody) is virtually identical in size with the 37 Kd protein we expressed, banding in the same place on the gel.

Finally, a small amount of the expressed protein was electroluted out of an SDS polyacrylamide gel and subjected to N-terminal sequence analysis. The amino acid sequence obtained was consistent with the predicted amino acid sequence of the λLC cDNA sequence of FIG. 4.

The human lipocortin which we expressed inhibited exogenous phospholipase A2 in the in vitro assay described in Example A above. This inhibition was detected first using crude lysates and later with a more purified preparation of expressed protein. When the soluble fraction of crude lysates prepared with a french pressure cell was assayed for phospholipase inhibitory activity, we obtained the results shown in Table I below. Inhibitory activity was detected in *E.coli* lysates containing plasmid pLiptrc155A, while no activity was detected in lysates from *E.coli* that did not contain the plasmid. As determined by gel analysis, the only difference between these two extracts was the presence of the 37 Kd protein in the inhibitory fraction. We found that the 37 Kd protein accounted for less than 1% of the total protein in the lysate. We also obtained similar results when sonicated lysates were assayed.

Although inhibitory activity could be detected directly in the soluble lysate, most of the 37 Kd protein in E.coli was insoluble and hence removed by low speed centrifugation after the cells were lysed with the french press. The insoluble protein was extracted from particulate matter with guanidine hydrochloride, dialyzed against 1M urea, and then assayed for phospholipase inhibitory activity. The results of this assay are shown in Table II below. The dialysate contained approximately 200 U of inhibitory activity per ml (1 U inhibits 15 ng A2). To insure that this activity was the result of a protein, and not some other component in the extract such as lipid, 25 μl of the lysate used in Table II were incubated with trypsin. As shown in Table III below, the inhibitory activity was very trypsin-sensitive.

Table I

Phospholipase Inhibit Activity in Crude E. coli Lysates.

Cultures of the W311101Q strain of E. coli, which either did or did not contain the plasmid pLiptrc155A, were induced with IPTG and lysed with a french pressure cell. Particulate matter was removed by centrifugation at 10,000×g for 20 min. The soluble fraction was assayed for phospholipase inhibitory activity. The numbers shown are the averages from several assays in which 50 μl of extracts were assayed with 100 ng of porcine pancreatic phospholipase $A_2$.

| Sample | Percent Inhibition |
|---|---|
| $A_2$ alone | 0 |
| $A_2$ + E. coli, no plasmid | 0 |
| $A_2$ + E. coli containing trc plasmid | 24 |

Table II

Dose-Response Curve Of Partially Purified Inhibitor

The insoluble preparation, which was recovered from JA221 cells transformed with pLiptrc155A (using the lysis treatment described above) was exposed to 6M guanidine hydrochloride in 25 mM sodium acetate (pH 6.0). Particulate matter was removed by centrifugation (100,000,000×g for 1 h). Extracted protein, which was highly enriched for the human 37 Kd protein, was dialyzed against 1M urea in 25 mM sodium acetate (pH 6.0) and then assayed for phospholipase $A_2$ inhibitory activity.

| μl extract assayed | Percent Inhibition |
|---|---|
| 0 | 0 |
| 3 | 12 |
| 10 | 26 |
| 30 | 58 |

Table III

Trypsin Sensitivity Of Inhibitor.

The partially purified preparation described in Table II was exposed to trypsin for 15 min at room temperature and then assayed with 100 ng of porcine pancreatic phospholipase $A_2$. Under the conditions used, the trypsin treatment did not alter the phospholipase $A_2$ activity. For each sample, 25 μ of inhibitor were assayed.

| Sample | Trypsin μg/ml | Percent Inhibition |
|---|---|---|
| $A_2$ alone | 0 | 0 |
| $A_2$ + inhibitor | 0 | 54 |
| $A_2$ + inhibitor | 1 | 3 |
| $A_2$ + inhibitor | 3 | 4 |

In addition to pLiptrc155A, we constructed other high level expression vectors of this invention. For example, plasmid pLipPLT4A was constructed as follows' plasmid pPLT4HTNF, a gift from Walter Fiers, (this plasmid is identical to the plasmid deposited in the culture collection of the Deutsche Sammlung Von Mikroorganismen, in Gottingen, West Germany, on December 27, 1984 under DSM No. 3175 and which was deposited within E.coli strain C600 and designated as pBR322-pL-T4-hTNF) was digested with restriction enzymes ClaI and HindIII and a linear fragment was obtained. Plasmid pL9/20 was partially digested with HindIII and then completely with EcoRI, and the 1350 bp fragment was isolated from an agarose gel. These two fragments were ligated in the presence of a ClaI-EcoRI linker containing an initiation ATG and the sequence coding for five amino acids 5' to the EcoRI site in the lipocortin cDNA. In the resulting expression vector, the $P_L$ promoter directs the transcription of a hybrid mRNA including sequences of $P_L$, $T_4$ and the lipocortin mRNA. Translation of this mRNA initiates at the first ATG of the human lipocortin coding sequence, resulting in a 37 Kd protein. A second tetracycline resistant plasmid pLipPLT4T was constructed by inserting the tetracycline resistance gene of pBR322 into the ScaI site of pLipPLT4A.

We transformed E.coli strains MCI061 and C600pCi 857 with pLipPLT4A and determined expression by SDS polyacrylamide electrophoresis and Western blot analysis as described above. The E.coli extracts showed a 37 Kd protein reactive with antibody to rat lipocortin.

E. EXPRESSION OF HUMAN LIPOCORTIN PROTEIN IN YEAST

Figure 7:
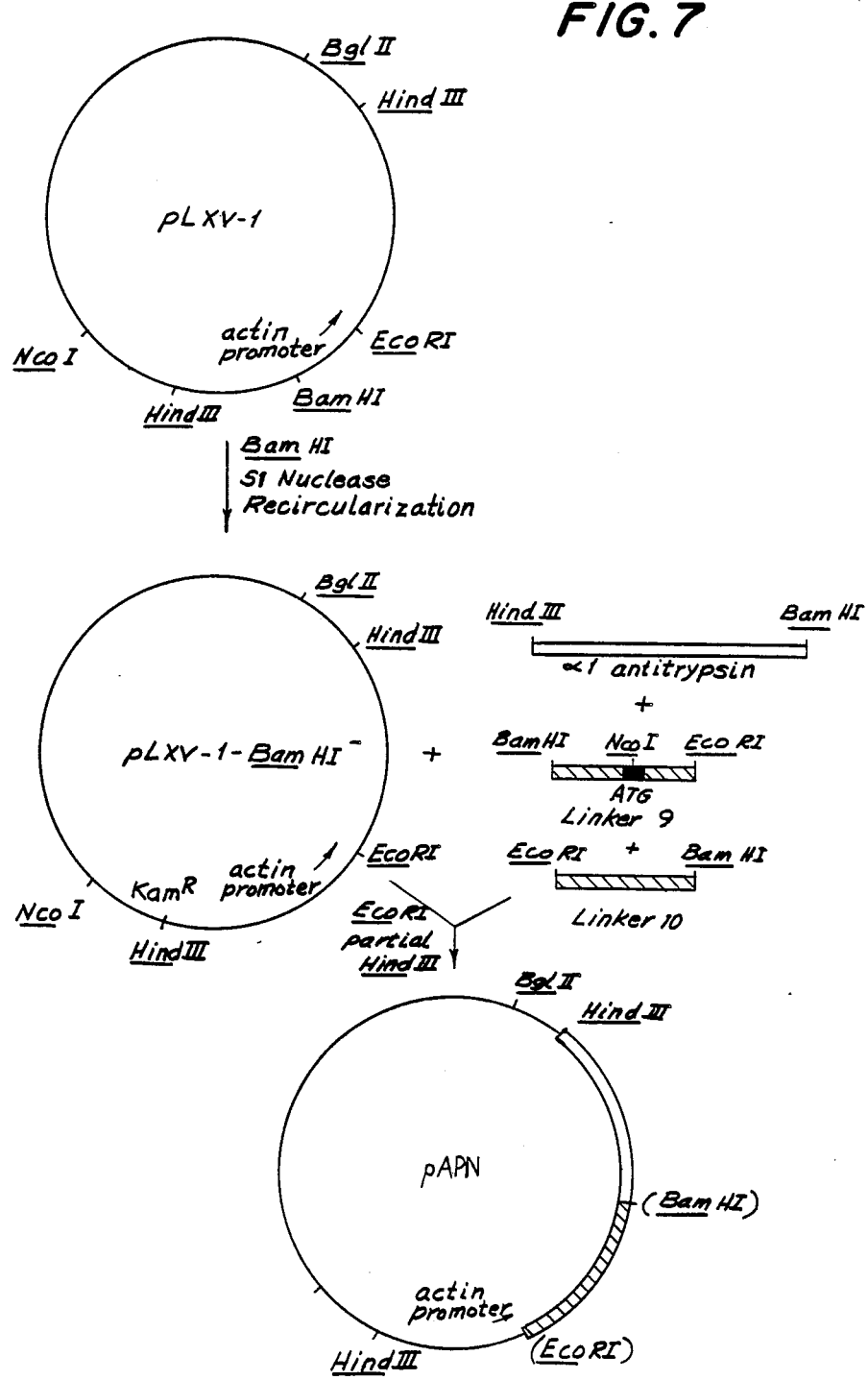
FIGS. 7-9 depict the construction of plasmid pBg120, a yeast expression vector for production of human lipocortin according to one embodiment of this invention.
Figure 8:
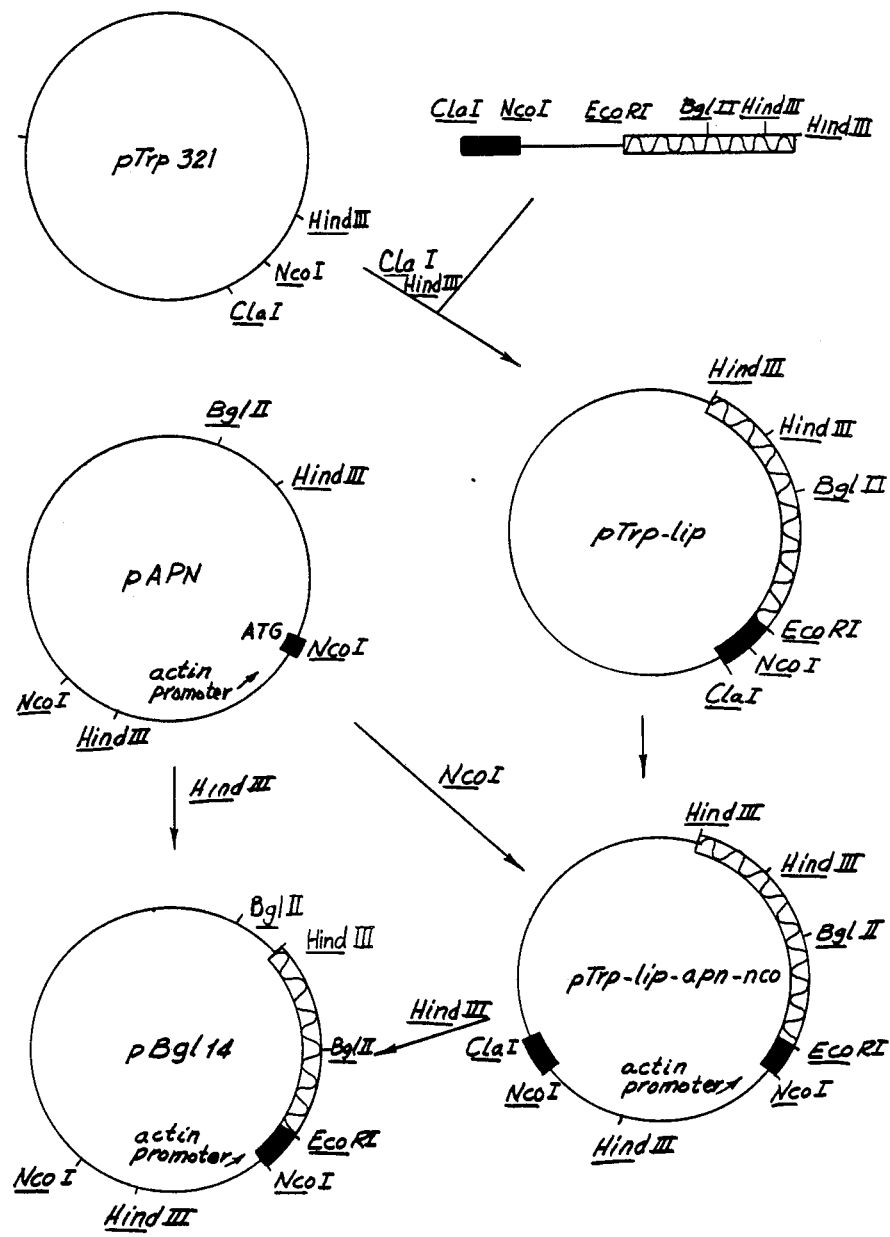
Figure 9:
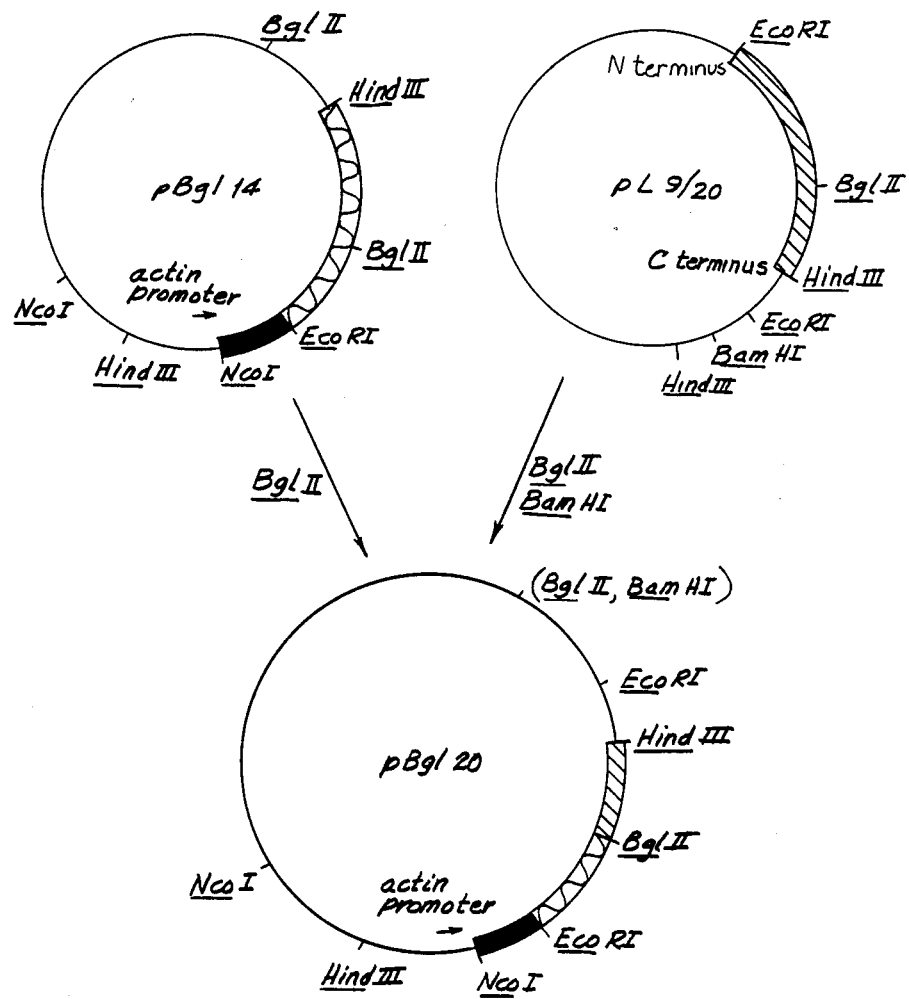

We have also constructed expression vectors for the production of human lipocortin in yeast. FIGS. 7–9 show the construction of pBg120 which, when used to transform yeast cells, expressed human lipocortin as detected by Western blot analysis with the anti-rat lipocortin antibody We constructed pBg120 as follows:

Plasmid pLXV-1 contains the origin of DNA replication from E.coli plasmid pBR322 and from yeast plasmid 2μ DNA. It can therefore replicate in both E.coli and yeast (J. Ernst, personal communication) We removed the BamHI site from plasmid pLXV-1 by digestion with BamHI, treatment with S1nuclease at 37° C. for 30 minutes and recircularization with T4 DNA ligase (FIG. 7). E.coli JA221 was transformed with the ligation mixture and plasmid pLXV-1-BamHI⁻ was isolated.

In order to reconstitute the ATG initiation codon of the acting gene on pLXV-1, we digested pLXV-1-BamHI⁻ with EcoRI and with HindIII. We isolated the large fragment containing the actin promoter We ligated together this fragment with a DNA fragment containing the human 1 antitrypsin gene containing a BamHI end and a HindIII linker* and two synthetic linkers (linkers 9 & 10).** Linkers 9 and 10 both contained EcoRI and BamHI sticky ends and linker 9 contained an NcoI restriction site and the ATG initiation codon. This ligation resulted in the loss of the EcoRI and BamHI restriction sites. We transformed *E.coli* JA221 with this ligation mixture and selected for Ampicillon resistance and Kanamycin resistance to insure the recreation of the HindIII site located within the Kam®️ gene. We designated the resultant plasmid pAPN.

*We used the α1 antitrypsin DNA fragment solely to insert the BamHI and HindIII restriction sites into the plasmid. The DNA sequence coding for α1 antitrypsin, between the two restriction sites, was later excised and replaced with the lipocortin DNA sequence. The specific sequence used to provide this restriction sites in the plasmid was irrelevant and any DNA sequence could have been used in place of the α1 antitrypsin DNA.*

**Linker 9 was a mixture of the two sequences AATTAACAATGG and AATTAACCATGGAG. Linker 10 was a mixture of GATCCT-CCATGGTT and GATCTTCCATTGTT.

FIG. 8 shows the insertion of the DNA sequences coding for human lipocortin into a yeast expression vector. The human lipocortin sequence was cloned in two parts. First, the N-terminal region was inserted behind and operatively linked to the yeast actin expression control sequence. Plasmid pTrp321 (R. Devos et al., "Molecular cloning of human interleukin 2 cDNA and its expression in *E.coli*," *Nucleic Acids Research*, 11, pp. 4307–23 (1983)) was digested with ClaI and HindIII and the large fragment was ligated to the pL9/20 1090-linker fragment prepared supra. p. 34. We isolated plasmid pTrplip by screening for the expression of human lipocortin as described above.

We next digested pAPN with NcoI and isolated the small fragment containing the yeast actin expression control sequence. We ligated this fragment to pTrp-lip which had been linearized with NcoI. We designated this plasmid pTrp-lip TM apn-nco. We digested ptrp-lip-apn-nco with HindIII and isolated the fragment containing the yeast actin expression control sequence and the DNA sequences corresponding to the N-terminal region of the human lipocortin. We ligated this fragment to the large HindIII fragment of pAPN to produce plasmid pBg114.

We obtained the DNA sequences corresponding to the remaining C-terminal fragment of the human lipocortin from the 800bp BglII-BamHI fragment of pL9/20, supra (FIG. 9). We digested pL9/20 with BglII and BamHI and electroeluted the 800bp fragment. This fragment was ligated to pBg114 which had been digested with BglII. We isolated plasmid pBg120, containing DNA sequences coding for human lipocortin operatively linked to the actin expression control sequence.

Figure 10:
FIG. 10 depicts an SDS-polyacrylamide gel analysis of crude yeast lysates. Lane a contains purified human lipocortin made in E. coli according to this invention. Lane b contains extracts from yeast with no plasmid. Lane d contains extracts from yeast containing pBg120. Lanes c and e contain extracts from yeast containing other plasmids without DNA sequences encoding human lipocortin.

We detected in extracts of yeast transformed with pBg120 a 37 Kd protein not observed in untransformed yeast cells or in yeast cells transformed with plasmids which did not contain the human lipocortin gene. This protein corresponded exactly on SDS-polyacrylamide gel electrophoresis to the human 37 Kd protein produced in *E.coli* (FIG. 10).

In yeast the human 37 Kd protein is produced as a soluble protein. It accounts for about 4% of the total cellular protein. When yeast cultures containing the recombinant protein were lysed with a french pressure cell at 20,000 p.s.i. and particulate matter removed by centrifugation (10,000×g, 10 min) approximately 80% of the inhibitory activity was recovered in the soluble fraction. The distribution of inhibitory activity correlated exactly with the distribution of the human protein based on SDS-polyacrylamide gel analysis. The recombinant protein produced in yeast has a blocked amino-terminus.

F. EXPRESSION OF HUMAN LIPOCORTIN PROTEIN IN MAMMALIAN CELLS

Figure 11:
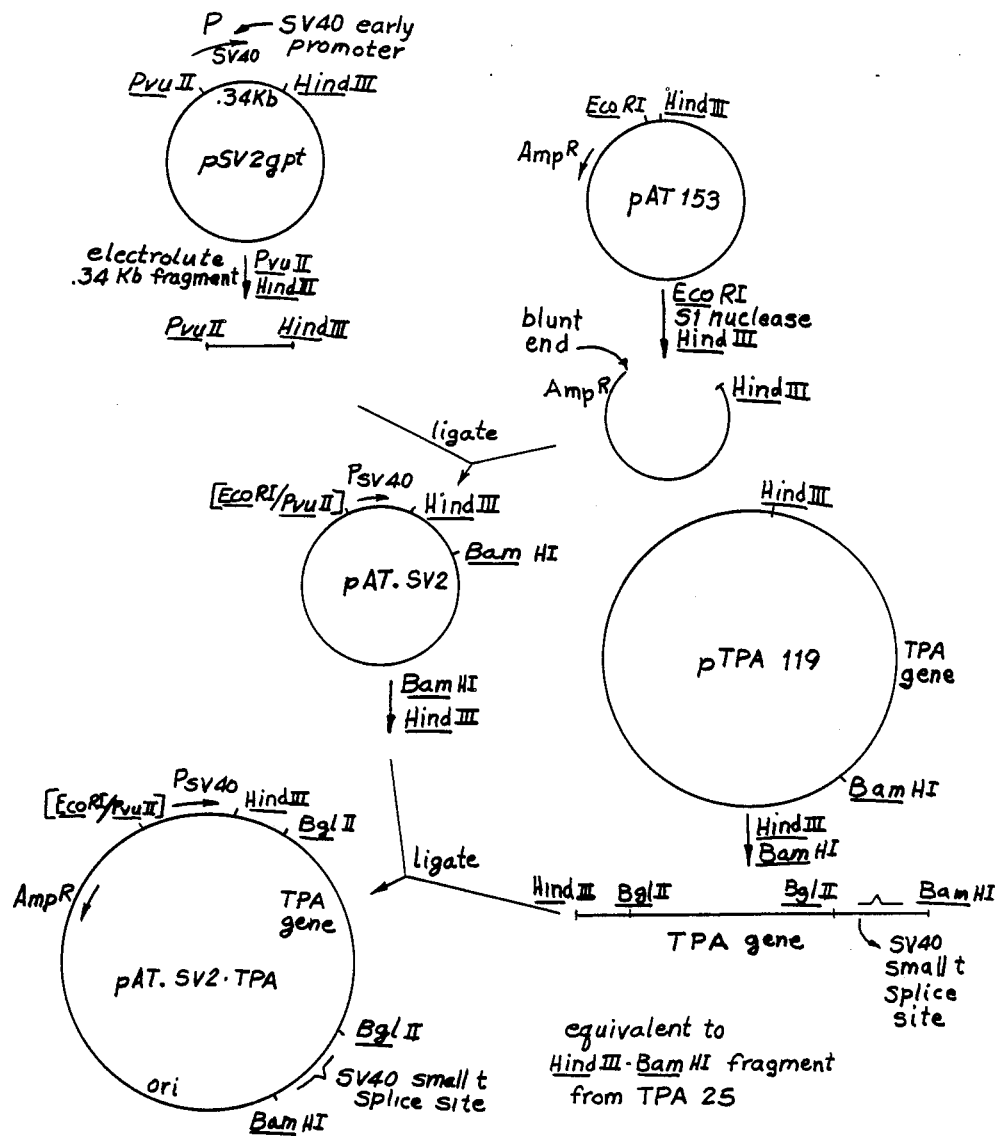
FIGS. 11-13 depict the construction of plasmid pSVL9109, a mammalian expression vector for production of human lipocortin according to one embodiment of this invention.
Figure 12:
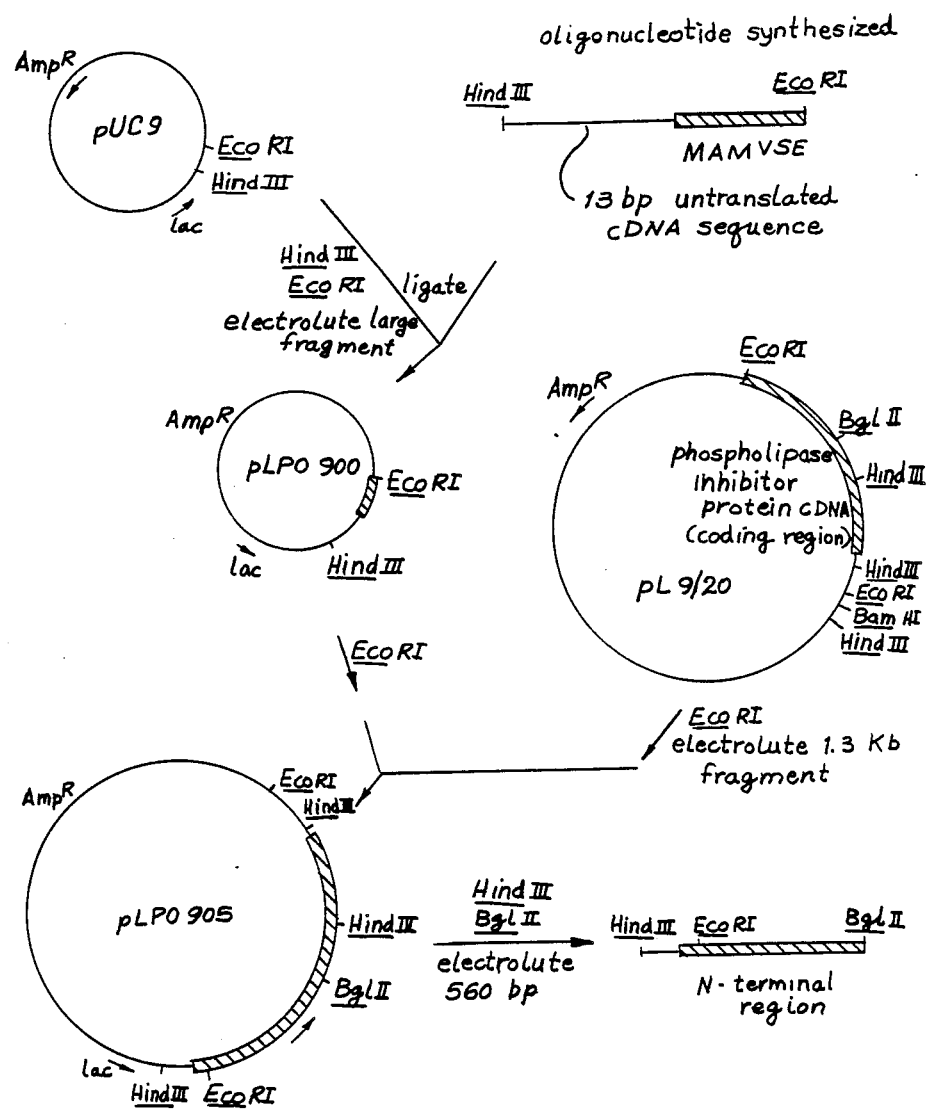
Figure 13:
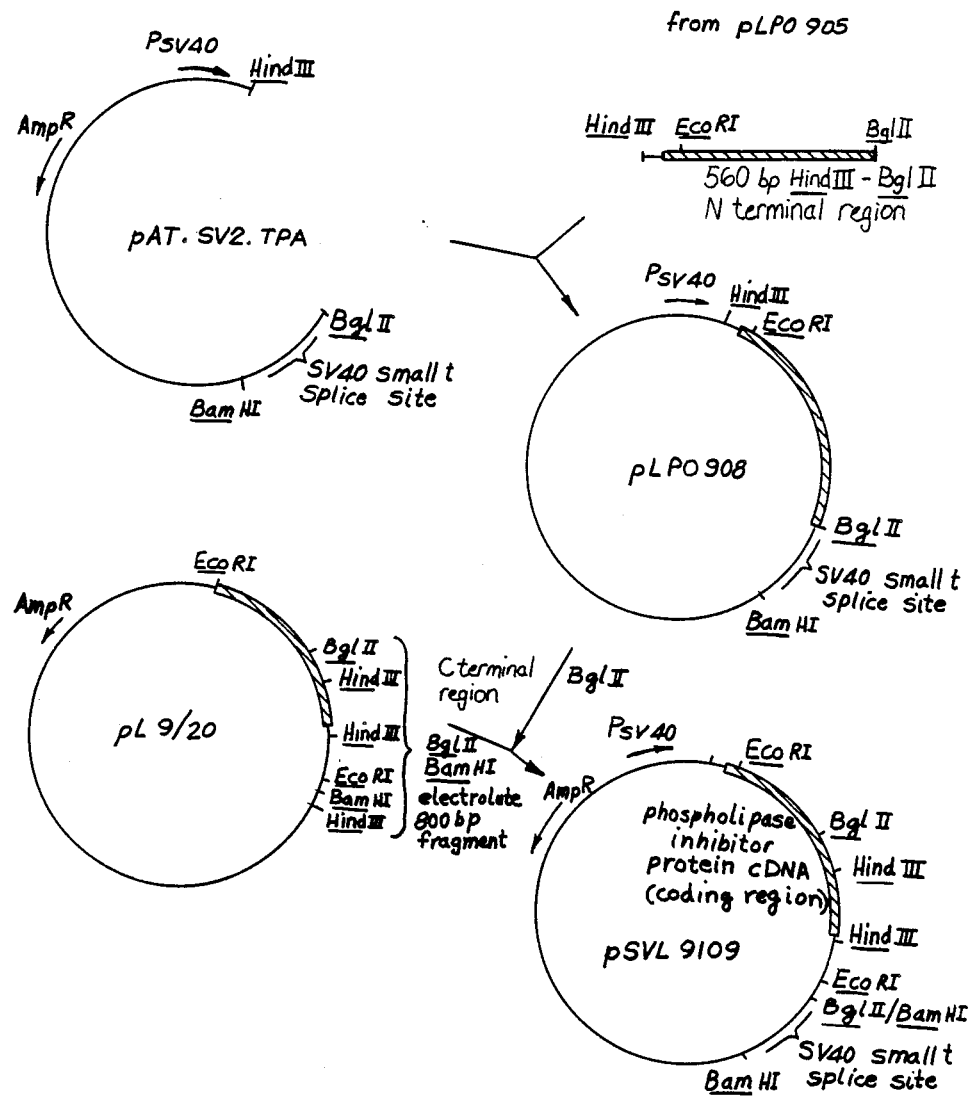

We have also constructed expression vectors for the production of human lipocortin in mammalian hosts. FIGS. 11–13 show the construction of pSVL9109 which, when transfected into cos and CHO host cells by the CaPO$_4$ procedure (F. Graham et al., *J. Virology*, 52, pp. 455–56 (1973)), expressed human lipocortin as detected by Western blot analysis with the anti-rat lipocortin antibody. We detected a 37 Kd immunoreactive protein not observed in nontransfected cells, indicating that the vector was producing the human inhibitor protein. We constructed pSVL9109 as follows:

As shown in FIG. 11, plasmid pSV2gpt (R. Mulligan et al., *Proc. Natl. Acad. Sci. USA*, 78, pp. 2072–76 (1981)) was cut with PvuII and HindIII and the 340 bp fragment containing the SV40 early promoter was isolated and inserted into pAT153 which had been previously cut with EcoRI, S1 treated, and then cut with HindIII. The resulting plasmid pAT.SV2 contained the promoter. This plasmid was then cut with HindIII and BamHI. Into this site we cloned a sequence which contained the small t splice site. This sequence was isolated from another plasmid, pTPA119, by cutting with HindIII and BamHI. The 3 kb insert contained the DNA sequence coding for human tissue plasminogen activator along with the small t splice site. This sequence is equivalent to that found in the pTPA25 HindIII-BamHI segment deposited with the American Type Culture Collection in Rockville, Md., on Aug. 21, 1984 under ATCC No. 39808. The HindIII-BamHI 3 kb piece was ligated to pAT.SV2 to yield plasmid pAT.SV2.TPA. This vector contains the SV40 early promoter followed by a HindIII site and the SV40 small t splice signal preceded by a BglII site.

We next inserted the coding sequence for human lipocortin into pAT.SV2.TPA. An oligonucleotide of 29 bp with EcoRI and HindIII ends was synthesized (see FIG. 12). This oligonucleotide includes the coding sequence for the first six amino acids of human lipocortin. This sequence was cloned into pUC9 (J. Vieira et al., Gene, 19, pp. 259–68 (1982)) which had been digested with EcoRI and HindIII to yield pLP0900. This plasmid was cut with EcoRI and treated with calf alkaline phosphatase. We then cloned the 1.3 kb EcoRI fragment from pL9/20 which corresponds to the coding region for human lipocortin into pLP0900. The resulting plasmid pLP0905 contains the entire coding region for human lipocortin with a HindIII site upstream (see FIG. 12). This makes the gene suitable for cloning behind the SV40 promoter of pAT.SV2.TPA.

FIG. 13 shows the insertion of the gene for human lipocortin into pAT.SV2.TPA to form a mammalian expression vector of this invention. The human lipocortin sequence was cloned into the expression vector in two parts. First, the N-terminal region was inserted behind the SV40 promoter and then the C TM terminal region was added. The plasmid pLP0905 was cut with HindIII and BglII and the 560 bp fragment containing the N-terminal region of human lipocortin was isolated. pAT.SV2.TPA was cut with HindIII and BglII and the 5 kb fragment containing the vector was isolated, free of TPA sequences. Into this HindIII-BglII vector, we inserted the 560 bp HindIII-BglII fragment containing the N-terminal region of human lipocortin to yield the plasmid pLP0908.

The C-terminal region of human lipocortin is found within the 800 bp BglII-BamHI fragment of pL9/20. Thus, pL9/20 was cut with BglII and BamHI, followed by electroelution of the 800 bp fragment. This fragment was ligated into the plasmid pLP0908 which had been cut with BglII and treated with calf alkaline phosphatase. Plasmid pSVL9109 was isolated. This plasmid has the entire human lipocortin coding sequence downstream of the SV40 early promoter followed by the SV40 small t splice signal. Plasmid pSVL9109 was used to transfect cos and CHO hosts as described above.

Thus, utilizing the DNA sequences of the invention, we have constructed high level expression vectors for the expression of human lipocortin in a biologically active form.

Recombinant DNA sequences prepared by the processes described herein are exemplified by a culture deposited in the culture collection of In Vitro International, Inc., Ann Arbor, Mich. The culture was deposited on Jan. 9, 1985 and is identified as follows:

λLC: IVI No. 10042

Microorganisms prepared by the processes described herein are exemplified by a culture deposited in the above-mentioned depository on Mar. 12, 1985 and on Aug. 14, 1985, respectively, and identified as follows:

*E.coli* W3110I$^Q$ (pLiptrc155A): IVI No. 10046
*S.cerevisiae* 331-17A (pBg120): IVI No. 10088.

G. PRODUCTION OF BIOLOGICALLY ACTIVE HUMAN LIPOCORTIN-LIKE POLYPEPTIDE FRAGMENTS

The production of polypeptide fragments smaller than the 37,000 molecular weight human lipocortin which display phospholipase inhibitory activity is highly desirable. A smaller polypeptide is more easily delivered to target cells by, e.g., transdermal infusion rather than intravenous injection. A smaller polypeptide might also have a more stable conformation than the 37K protein. For example, the N-terminal end of the 37K protein contains a cluster of hydrophobic amino acids, which may cause the formation of intermolecular aggregates, while the C-terminal end contains four cysteines capable of forming improper disulfide linkages (see FIG. 4). Thus removal of the N-terminal and C-terminal ends of the large protein may avoid conformational heterogeneity when the protein is produced in high concentrations. Isolation of biologically active fragments will also permit better characterization of the active site of the lipocortin molecule and lead to the design of fragments with optimal therapeutic value.

Although a variety of methods can be used for generation of polypeptide fragments from their parent molecule in accordance with this aspect of our invention, we chose to subject the human lipocortin-like polypeptide to limited protease digestion in the illustrative embodiment described below. We first optimized digestion conditions for each protease so that the fragments generated were few in number, usually less than ten, and therefore easily isolated. The optimum conditions were in general determined by the following factors: (1) the type of protease used; (2) the physical state of the target protein, i.e., denaturing or non-denaturing conditions; (3) the time period for digestion; (4) the temperature; (5) the amount of protease used; and (6) the pH.

We used two different types of proteases to digest our 37K lipocortin-like polypeptide. The first type hydrolyzes peptide bonds non-specifically. This type is represented by elastase and proteinase K proteases. The second type, represented by the proteases plasmin and thrombin, hydrolyzes a specific peptide bond. This second type probably recognizes target proteins both by amino acid sequence and by conformation surrounding the cleavage sites. We also used trypsin, a third type of protease, to localize the C-terminal end of the active peptide fragments (see pp. 48–49, infra). Trypsin hydrolyzes peptide bonds at specific amino acids. Other proteases of this type include chymotrypsin and V8 protease. Because we wished to obtain fragments with biological activity, we performed digestions under non-denaturing conditions.

Figure 14:
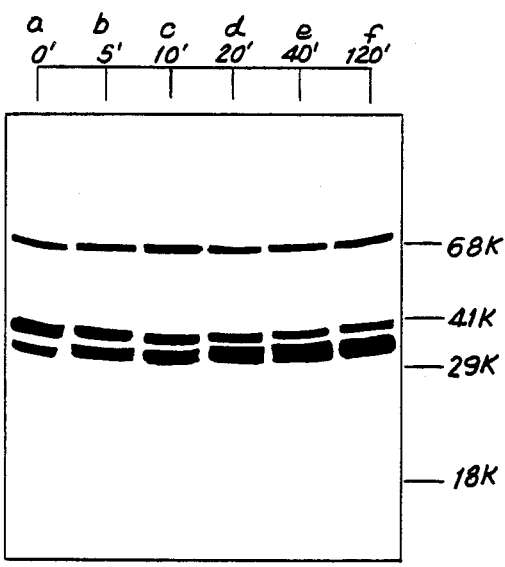
FIG. 14 depicts an SDS-polyacrylamide gel analysis of plasmin digested human lipocortin-like polypeptide. Lanes a-f represent samples taken at 0, 5, 10, 20, 40 and 120 minutes, respectiVely, after addition of plasmin.

1. Production, Isolation And Characterization Of Plasmin-Digested Fragments From Recombinant Human Lipocortin In order to optimize conditions for plasmin digestion, we incubated an aliquot of our *E.coli*-produced human lipocortin-like polypeptide (100 μg) in 100 μl of 0.2M Tris HCl (pH 8.0), 5 mM EDTA and 0.1 mg bovine serum albumin/ml solution with 10 μl (1 μg/μl) plasmin (Calbiochem) at room temperature. At different time intervals, 15 μl were withdrawn and the reaction quenched by adding 5 μl of buffer containing 8% SDS and then boiling the aliquots for 5 min. The digestion mixture at each time point was analyzed by SDS gel electrophoresis. The results, depicted in FIG. 14, show that after an hour of incubation almost all the protein was digested to a fragment with a molecular weight of 33,000. This 33K fragment was resistant to further digestion either with longer incubation times or in the presence of increased amounts of plasmin.

Figure 15:
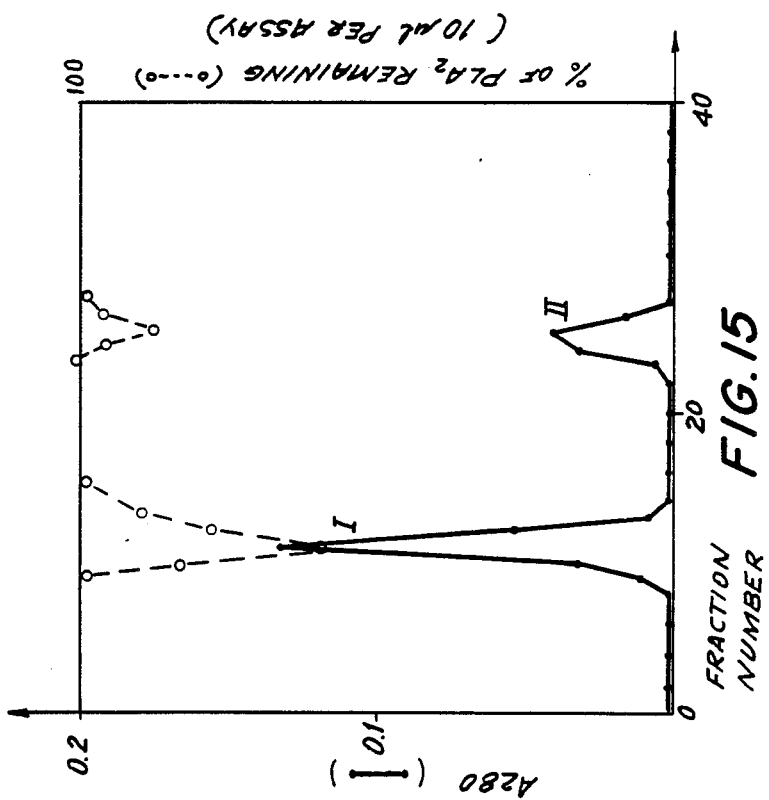
FIG. 15 depicts the phospholipase $A_2$ inhibitory activity of the plasmin fragments of human lipocortin-like polypeptide after fractionation by Biogel P-60 column chromatography.

Using the digestion conditions described supra. we incubated 500 μg of human lipocortin-like polypeptide with 75 μg of plasmin for 1 hour. The reaction was stopped with 250 KIU of the protease inhibitor aprotinin (Sigma). We loaded the digested samples onto a Biogel P-60 column (1.0×50 cm), equilibrated with 0.2M Tris-HCl, pH 7.5, 5 mM EDTA, 0.1% bovine serum albumin at 4° C. We collected 1.1 ml fractions. The elution profile of fragments monitored at 280 nm disclosed two protein peaks (FIG. 15). We analyzed aliquots of fractions from each peak by high pressure liquid chromatography and by SDS gel electrophoresis. The results showed that peak I contained a fragment with 33,000 molecular weight (designated as Lipo-L), and peak II contained a fragment with 4,000 molecular weight (designated as Lipo-S).

Fractions of the Biogel P-60 column chromatography were assayed for phospholipase $A_2$ inhibitory activity, as described supra. The majority of activity was associated with peak I (FIG. 15). Although a small amount of inhibitory activity was detected in peak II, that activity was not dependent on fragment concentration and was probably caused by non-specific binding of the fragment to the membrane.

We also isolated the two cleavage products by reverse phase high pressure liquid chromatography with a gradient of acetonitrile from 0–75% in 0.1% trifluoroacetic acid using $C_4$ column chromatography (Vydac). Lipo-S was eluted with 38% acetonitrile and Lipo-L with 48% acetonitrile.

We determined the N-terminal amino acid sequence of Lipo-L (33K; peak I) by sequential Edman degradation using a gas phase sequencer (Applied Biosystems 470A). PTH-amino acids were analyzed by high pressure liquid chromatography on a 5 μm cyanocolumn (Hypersil) using a gradient of acetonitrile methanol (4:1) from 15-55% in 0.02M sodium acetate buffer (pH 5.7). We determined the N-terminal amino acid sequence of Lipo-L to be $H_2N$-Gly-Gly-Pro-Gly-Ser-Ala-Val. The N-terminal glycine of Lipo-L corresponds to Gly-30 of the 37K protein.

To determine the C-terminal amino acid sequence of our fragments, we compared the tryptic peptide map of the 37K rat lipocortin (FIG. 16) with a tryptic peptide map which we generated for each of the fragments. We diluted 20 μl of the 37K lipocortin-like polypeptide (40 μg) in 0.2M Tris-HCl, pH 8.0, 5 mM EDTA, 0.1 mg/bovine serum albumin/ml with 0.2 ml of 0.1M $NH_4HCO_3$ plus 1 mM $CaCl_2$. The mixture was then incubated with trypsin for 24 hr. at 37° C. . During this incubation, we added trypsin at three time points: 0.5 μg at time zero, 0.25 μg after 4 hr. and 0.25 μg after 19 hr. The digestion was stopped by adding 10 μl of 90% formic acid to the reaction mixture. We digested the plasmin fragments using identical conditions, except that we first dried down the fragments, which had been purified from high pressure liquid chromatography, with a Speedvac concentrator (Savant), and dissolved the residues in 0.1M $NH_4HCO_3$ and 1 mM $CaCl_2$.

We resolved the tryptic fragments by reverse phase high pressure liquid chromatography with a gradient of acetonitrile from 0-75% in 0.1% trifluoroacetic acid on a $C_{18}$ column (Spectraphysics). We then determined the amino acid sequence of each of the peak fractions. First, we established the amino acid composition of each peak by hydrolyzing the peptides in 6N HCl for 24 hr. and determining the composition on a Beckman 6300 amino acid analyzer. We compared the observed compositions with predicted compositions based on sequence data of all possible fragments from the 37K polypeptide and assigned identifications to each peak. We also determined the amino acid sequence of some of the peaks directly by sequence analysis.

Figure 17:
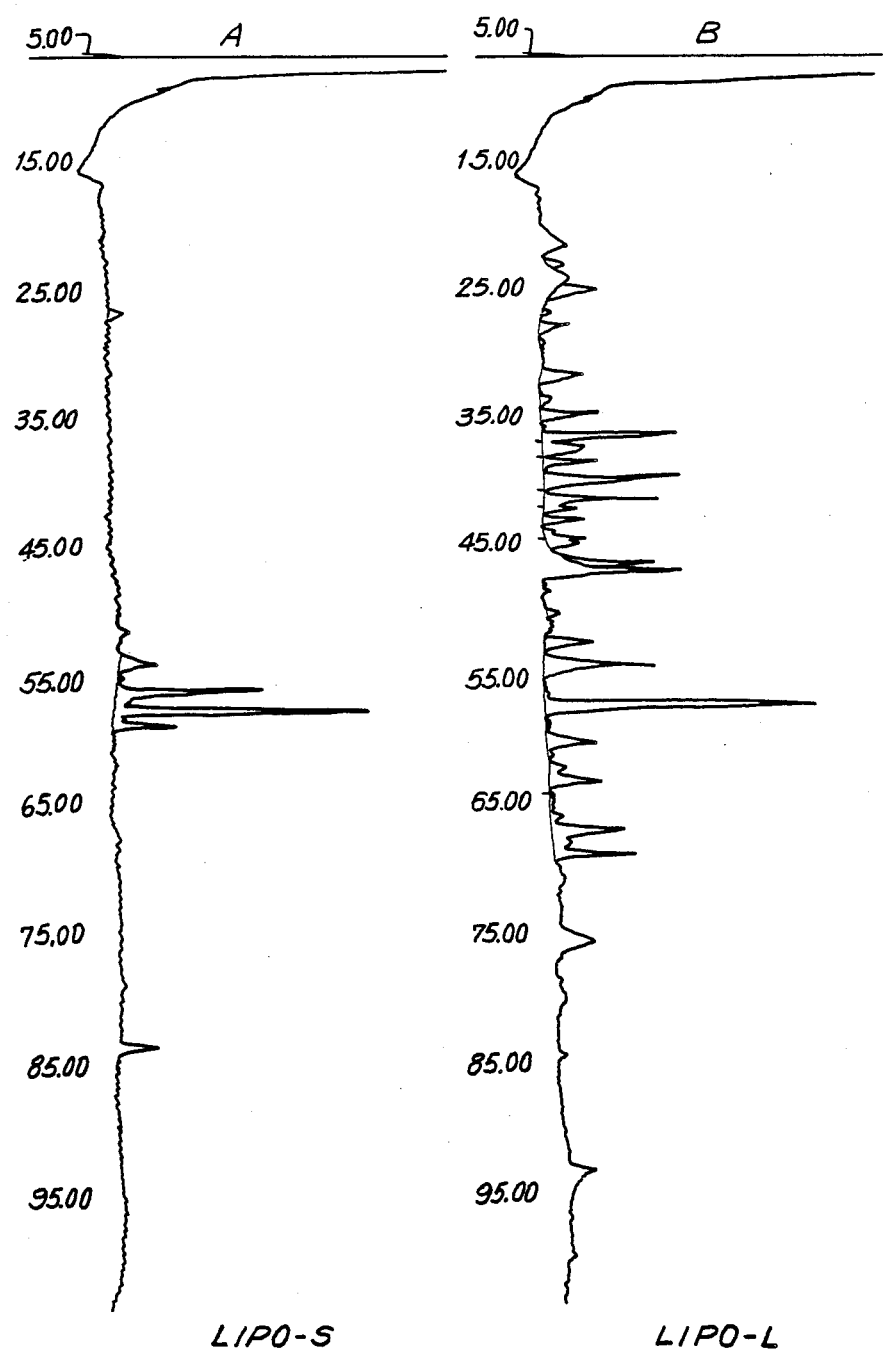
FIG. 17 depicts the amino acid sequences of fragments obtained from tryptic digestion of Lipo-S and Lipo-L.

By comparing the map of fragment Lipo-L (FIG. 17B) with that of 37K polypeptide (FIG. 16), we concluded that the biologically active Lipo-L fragment has the same C-terminal amino acid sequence as that of the 37K polypeptide. Therefore, this data, when combined with our N-terminal sequence data, demonstrate that Lipo L contains amino acid residues #30 to #346 of the 37K polypeptide. By comparing the peptide maps of fragment Lipo S (FIG. 17A) with that of the 37K polypeptide, we concluded that Lipo S contains amino acid residues #1 to 29 of the 37K protein.

2. Production, Isolation And Characterization Of Elastase Digested Fragments From Recombinant Human Lipocortin We treated 50 μl of the 37K human lipocortin-like polypeptide (75 μg), 0.2M Tris-HCl, pH 8.0, 5 mM EDTA, 0.1 mg bovine serum albumin/ml, with 2.5 μg (1 μg/l in 10 mM ammonium acetate, pH 6.0) of elastase (Sigma) at room temperature. We analyzed the digestion products at different time intervals as described supra to optimize conditions for elastase digestion. The results showed that 20 min. of incubation generated fragments with molecular weights ranging from 10K to 33K.

Figure 18:
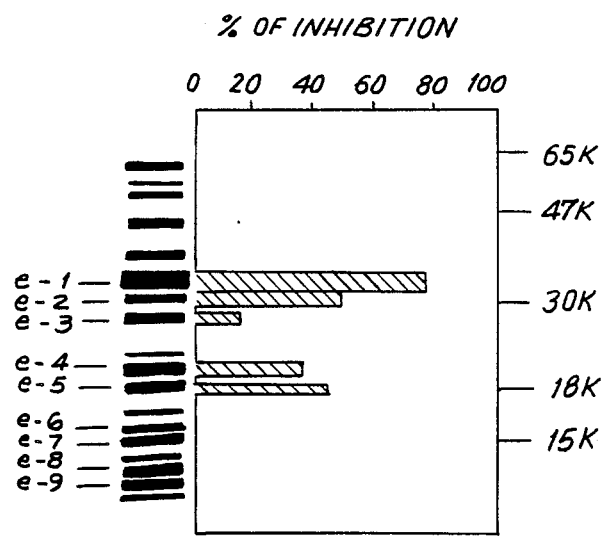
FIG. 18 depicts the phospholipase $A_2$ inhibitory activity of the elastase fragments of human lipocortin-like polypeptide after separation by SDS polyacrylamide gel electrophoresis.

We incubated 150 μg of the 37K polypeptide with 5 μg of elastase under optimum conditions as described above and subjected the digested polypeptides to SDS-polyacrylamide gel electrophoresis (D. A. Hager and R. R. Burgess, Anal. Biochem., 109, 76-86 (1980)). The polypeptide bands were visualized by soaking the gel in 0.25M KCl, 2mM DTT at 4° C. for 5-10 min. We then cut out the polypeptide bands and removed the KCl from the gel slices by soaking each slice in deionized $H_2O$ containing 2mM DTT for 10 min. at room temperature. The fragments were then eluted from the gel at room temperature for 2 hr. by a solution of 0.1% SDS; 0.2M Tris HCl, pH 7.5; 5 mM EDTA; 5 mM DTT; 0.01% bovine serum albumin. The fragments-containing solution was then mixed with a solution of ice-cold acetone at −70° C. and incubated for 30' at −70° C. . We collected the precipitate by centrifugation at 10,000 rpm (SS34 rotor) for 10 min. at 4° C. , and rinsed once with ice cold 80% acetone and 20% buffer containing 0.2M Tris HCl, pH 7.5 and 5 mM DTT. The precipitate was collected by centrifugation and dried under vacuum for 5-10 min. We then dissolved the dried powder in 6M guanadine hydrochloride in 0.2M Tris HCl (pH 7.9), 2 mM DTT, 5 mM EDTA, 0.1% bovine serum albumin for 20 min. To the solution we then added a "renaturation" buffer (20% glycerol and 80% 0.2M Tris-HCl (pH 7.9), 2 mM DTT, 5 mM EDTA, 0.1% bovine serum albumin). The solution was then allowed to stand at 4° C. overnight. We next assayed for phospholipase $A_2$ inhibitory activity as described. The activities of the SDS-gel fragments are shown in FIG. 18. The fragments e-1, e-2, e-3, e-4 and e-5, with molecular weights of 33K, 30K, 27K, 20K and 18K, respectively, showed phospholipase $A_2$ inhibitory activity.

We then purified the major active fragments (e-1, e-4, and e-5 of FIG. 18) by preparative SDS-gel electrophoresis. We visualized the polypeptide bands by soaking the gel in 0.25M KCl and excised the biologically active polypeptide bands. We electroeluted the fragments using standard techniques (M. W. Hunkapiller, E. Lujan, F. Ostrader and L. E. Hood, *Methods Enzymol.* 91, pp. 227-236 (1983)).

We determined the N-terminal and C-terminal amino acid sequences of e-1, e-4 and e-5. The purified fragments all showed the identical N-terminal amino acid sequence: $H_2N$-Gly-Gly-Pro-Gly-Ser-Ala-Val-Ser-Pro-Tyr. This N-terminal glycine corresponds to Gly-30 of the 37K protein.

Figure 19:
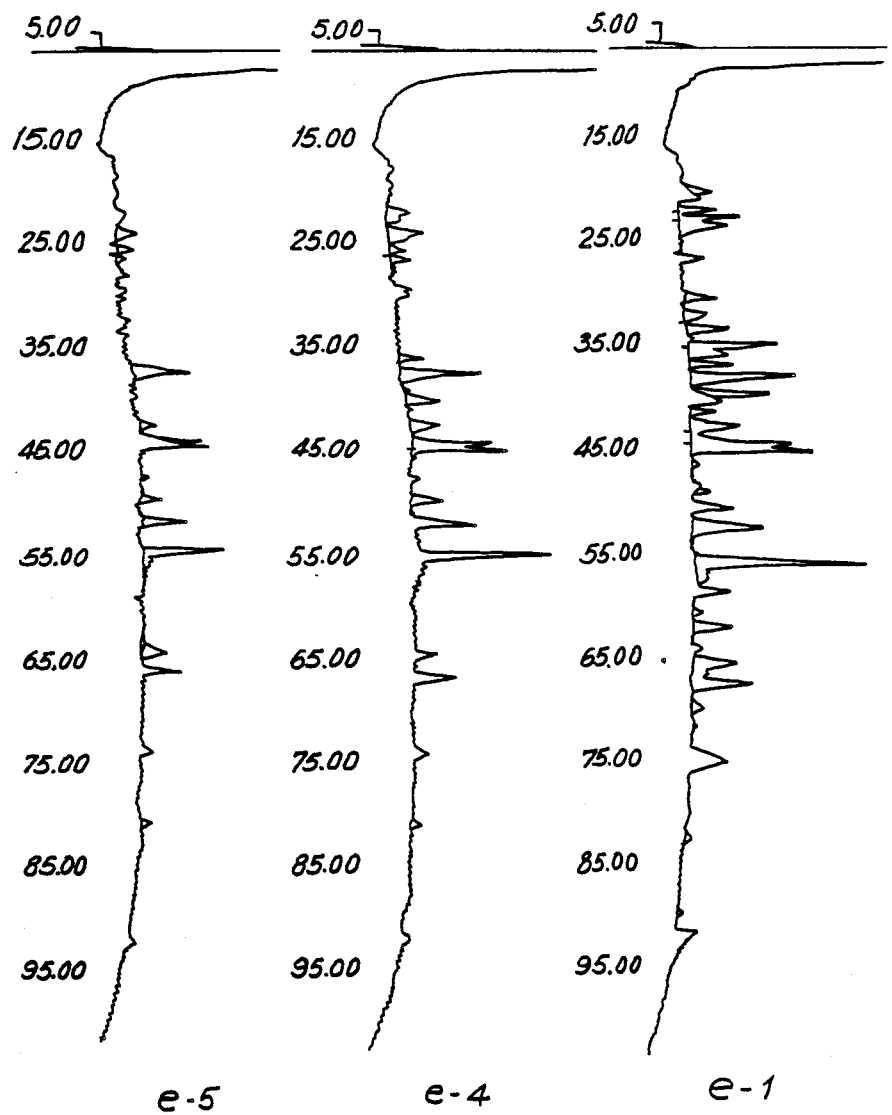
FIG. 19 depicts the amino acid sequences of fragments obtained by tryptic digestion of e-1, e-4 and e-5.

FIG. 19 shows the tryptic peptide maps of these purified fragments. We compared these maps with that of the 37K protein (FIG. 16) and found that the 18K e-5 fragment lacked the tryptic fragment Ala-Leu-Tyr-Glu-Ala-Gly-Glu-Arg (residues #205-212 of the 37K protein) and all fragments beyond this peptide. This suggests that cleavage is before this peptide. The peptide map contains the fragment Asn-Ala-Leu-Leu-Ser-Leu-Ala-Lys (residues #178-185 of the 37K protein). Thus, the C-terminus of this fragment is between Lys-185 and Arg-212 of the 37K protein. Similarly, the peptide map of the 20K e-4 fragment contains all the fragments found in the 18K fragment plus an additional peptide Ala-Leu-Tyr-Glu-Ala-Gly-Glu-Arg-Arg-Lys (residues #205-214 of the 37K protein). The C-terminal end of this fragment is therefore between Lys-214 and Arg-228 of the 37K protein. The C-terminal end of the 33K e-1 fragment is located between Lys-337 and Asn-346 of the 37K protein.

Thus, we have isolated at least three biologically active peptide fragments of the 37K lipocortin-like polypeptide. All three fragments have identical N-terminal ends, beginning with Gly 30 of the 37K polypeptide, each ending at a different point along the 37K molecule.

All three show the phospholipase A2 inhibitory activity of the full-size lipocortin-like polypeptide.

Although we used the above methods for production of polypeptide fragments from human lipocortin-like polypeptide produced in *E.coli*, it should be understood that such molecules can also be produced by a variety of other methods. For example, such molecules can be produced by proteases other than the ones we used or by chemicals which cleave or synthesize peptide bonds. Furthermore, such molecules can also be produced by expression of truncated DNA sequences coding for these fragments. However, this method may require different purification procedures for each fragment and occasionally results in the production of DNA sequences which are unstable in the expression vector.

H. THE PRODUCTION OF BIOLOGICALLY ACTIVE HUMAN LIPOCORTIN-LIKE POLYPEPTIDE FRAGMENTS BY RECOMBINANT DNA TECHNIQUES

An alternative method of generating lipocortin-like polypeptide fragments by recombinant DNA techniques is to introduce into the DNA sequence encoding lipocortin codons which, upon expression of the DNA sequence in the form of the polypeptide, result in sites at which the polypeptide can be cleaved (e.g., chemically or proteolytically). These codons can be introduced into the DNA by various techniques known in the art such as mutagenesis or insertion. Thus, an altered lipocortin-like polypeptide is produced by the host cell, purified in the same manner as the unaltered full length polypeptide and cleaved to yield a desired fragment or fragments. Using this strategy, we have altered the lipocortin DNA sequence of the present invention to produce altered polypeptides which when cleaved in vitro. yield lipocortin-like polypeptide fragments displaying phospholipase A2 inhibitory activity.

According to one embodiment of this technique, we constructed DNA sequences that code for altered lipocortin-like polypeptides by modifying the DNA sequence of lipocortin to introduce methionine codons into the sequence. Upon expression of this sequence in a host cell, altered lipocortin-like polypeptides were produced having either a specific amino acid replaced by a methionine or an inserted methionine at a particular site along the polypeptide sequence. Treatment of these altered polypeptides with cyanogen bromide, which cleaves polypeptides specifically at methionine residues, yielded lipocortin-like polypeptide fragments having phospholipase A2 inhibitory activity.

We have found that the natural human lipocortin protein has only two methionine residues (at amino acids 56 and 127) which are contained within the biologically active elastase fragments described in Example G(2) above. Since cleavage of a lipocortin-like polypeptide with cyanogen bromide inactivated the polypeptide and any fragments produced thereby, we inferred that one or both of these methionines were necessary for the biological activity of the protein. Thus, a preliminary step in the production of active lipocortin-like polypeptide fragments by cyanogen bromide treatment required the replacement of these two methionines with another amino acid without destroying the biological activity of the lipocortin protein. We therefore replaced methionines 56 and 127 with leucine residues and obtained a biologically active polypeptide fragment upon treatment with cyanogen bromide.

We replaced methionines 56 and 127 by mutagenesis of the DNA sequence encoding lipocortin as follows: We restricted plasmid pLiptrc155A, which contains the DNA sequence encoding lipocortin, with the restriction enzyme PvuI, resulting in a linearized pLiptrc155A molecule. We also restricted plasmid pKK233-2 with the restriction enzymes NcoI and HindIII, which cut the plasmid on either side of the DNA sequence encoding lipocortin (see Example D and FIG. 6 for the construction of these plasmids). Mixture of the two restricted plasmids, when denatured and reannealed, yielded a gapped heteroduplex with the DNA sequence encoding lipocortin in an approximately 1300 base pair single-stranded region. Mutagenic oligonucleotides Lipo 60 and 61 were phosphorylated at the 5' end and a 320-fold excess was added to the heteroduplex mixture. Lipo 60 and 61 contain DNA sequences similar to a portion of the lipocortin DNA sequence but having specific nucleotide changes such that expression of the oligonucleotide sequences results in the replacement of met 127 and met 56 of lipocortin with a leucine residue, respectively (see FIG. 20). These oligonucleotides therefore hybridize to the single-stranded region of the heteroduplex molecules. The DNA gaps in the heteroduplex molecules were filled in with the Klenow fragment of DNA polymerase I and the DNA ligated with T4 polynucleotide kinase [see, Morinaga, et al., *Biotechnology*, 2, pp. 636–39 (1984)]. We transformed *E.coli* strain JA221 with this DNA and selected for transformants by culturing the host cells on LB-ampicillin plates.

We screened the transformants for those colonies containing an altered lipocortin DNA sequence by hybridization with $^{32}$P-labeled oligonucleotides Lipo 60 and 61 as follows: We transferred the colonies to a nitrocellulose filter and placed the filter colony side up on a fresh LB-ampicillin plate. We incubated the plate for 4 h at 37° C. . We then transferred the filter to a fresh LB plate containing ampicillin and chloramphenicol (250 μg/ml) and incubated the plate overnight at 37° C. . We lysed the colonies with 0.5M NaOH-1.5M NaCl and neutralized the lysate twice with 0.5M Tris-HCl (pH 7.7)-1.5M NaCl. We baked the filters in a vacuum oven for 2 h at 80° C. and prehybridized them in 200 ml of 6×SSPE (0.9M NaCl, 90 mM sodium phosphate, 6 mM sodium EDTA, pH 7.0), 0.5% SDS, 100 μg/ml tRNA and 5x Denhardt's solution at 55° C. with shaking for several hours. We then hybridized the filters overnight at 55° C. in 200 ml of the prehybridization mixture containing 10 pmoles of $^{32}$P-labeled oligonucleotide. We washed the filters with 6xSSPE and detected hybridization by autoradiography [see T. Maniatis, et al., supra.

We isolated a number of positive clones by this procedure. One of these clones, designated Lipo 8, was grown up and its plasmid DNA, designated pLipo8, was extracted and sequenced according to the technique of Maxam and Gilbert, supra. This sequencing analysis showed that the desired nucleotide replacements, i.e., replacement of the DNA codons encoding met 56 and 127 with codons encoding leucine, had been achieved.

Figure 21:
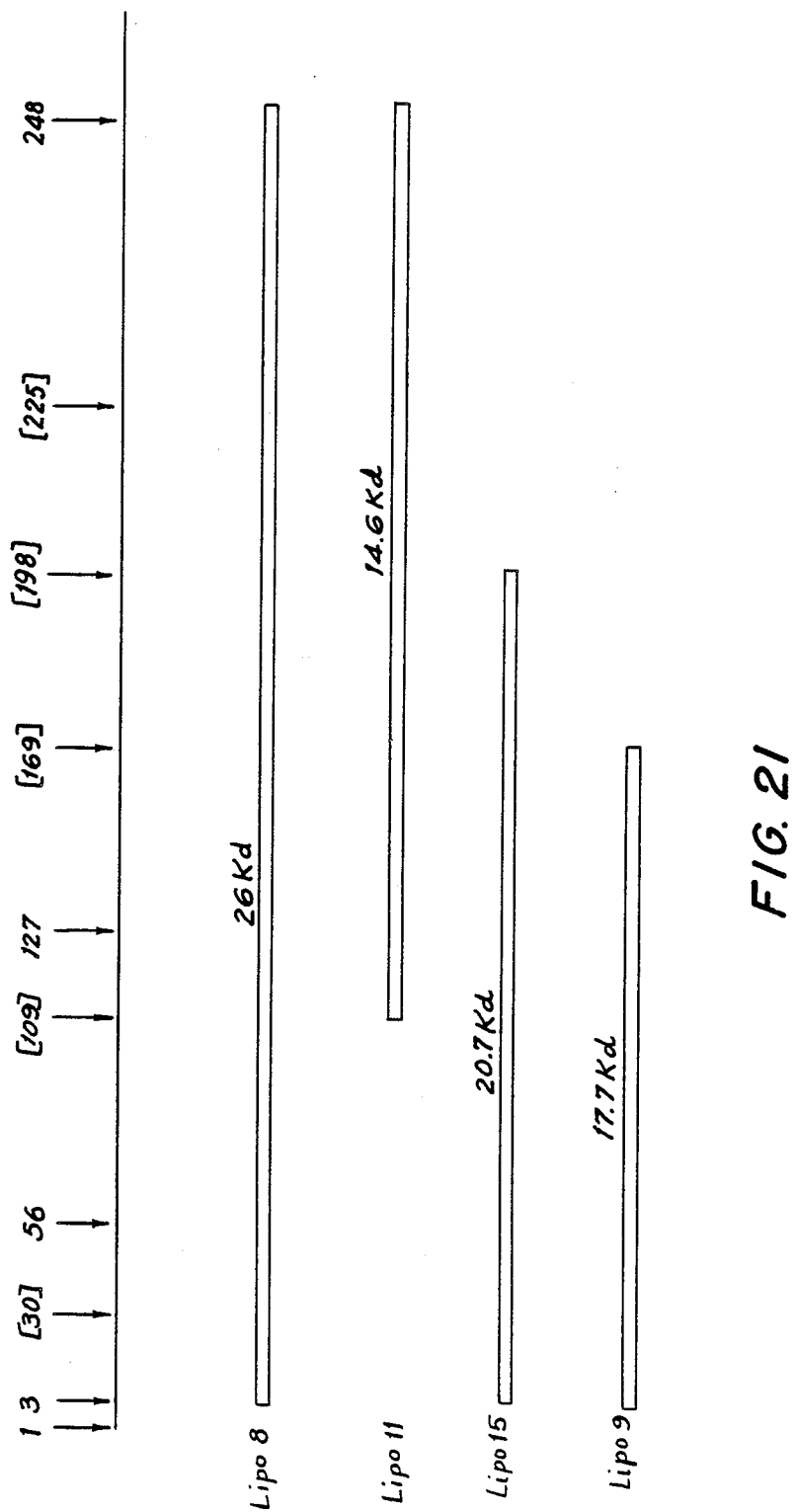
FIG. 21 is a schematic line map of the lipocortin amino acid sequence indicating by numbers the sites along the sequence where methionines are located. The bracketed numbers indicate sites where methionines can be introduced to yield fragments according to this invention. Several fragments of this invention and their molecular weights are depicted below the map.
Figure 22:
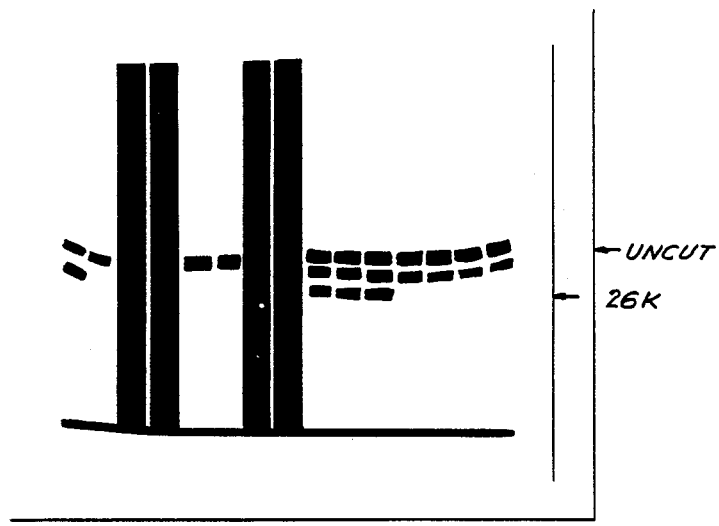
FIG. 22 depicts an SDS-polyacrylamide gel analysis of untreated and cyanogen bromide-treated human lipocortin-like polypeptide extracted from Lipo 8, showing a 26 Kd fragment.

We also extracted the expressed protein from Lipo 8 and treated this preparation with 3 mg/ml of cyanogen bromide in 70% formic acid to produce lipocortin-like polypeptide fragments. We tested this crude fragment mixture for phospholipase A2 inhibitory activity using the in vitro assay described earlier. Whereas wild-type lipocortin was inactivated by cyanogen bromide treatment for 1 h, the fragment mixture showed activity after 4 h of treatment. We then isolated a 26 Kd polypeptide fragment from this mixture by SDS-polyacrylamide gel electrophoresis (see FIGS. 21 and 22) and renatured the fragment as described in Example G(2) above. We tested this purified fragment for phospholipase $A_2$ activity using the in vitro assay and found that this large fragment of Lipo 8 displayed biological activity.

Once we had demonstrated the ability to replace met 56 and 127 without affecting the biological activity of the resulting lipocortin polypeptide fragment, we could then replace other amino acid residues of the lipocortin protein with methionine or insert methionines into various sites within the amino acid sequence of the lipocortin protein. In this way, new cleavage fragments of lipocortin with biological activity were isolated.

For example, using the procedure outlined above, we replaced the leucine at residue 109 of the amino acid sequence of lipocortin with a methionine. We hybridized mutagenic oligonucleotide Lipo 68 (see FIG. 20) to a heteroduplex formed from restriction of plasmids pKK233-2 and pLipo8 (which is identical to the pLiptrc155A of FIG. 6 except for the nucleotide changes of Lipo 60 and 61). We thus obtained a transformant, Lipo 11, that contains the desired nucleotide changes to replace Leu 109 with a methionine. pLipo11 DNA was extracted from this transformant and sequencing indicated the desired nucleotide changes had been achieved. Clone Lipo 11 was then grown up in culture and expressed protein extracted and treated with cyanogen bromide to produce fragments. We isolated a 14.6 Kd polypeptide fragment (see FIG. 21) by SDS-polyacylamide gel filtration of the treated protein extract [See Biorad Catalog/Price List K, p. 37 (1985)] and assayed this fragment for biological activity using the in vitro assay. This assay indicated that the Lipo 11 fragment possesses phospholipase $A_2$ inhibitory activity.

Similarly, oligonucleotide Lipo 78 (see FIG. 20) was used to generate a transformant, Lipo 15, which contains the desired nucleotide changes to replace Leu 198 with a methionine. Cleavage of the extracted expressed protein with cyanogen bromide followed by SDS-polyacrylamide gel filtration resulted in the purification of a 20.7K polypeptide fragment (see FIG. 21) which was then assayed for biological activity. This assay indicated that the Lipo 15 fragment possesses phospholipase $A_2$ inhibitory activity.

Alternatively, we inserted a methionine into the lipocortin amino acid sequence at residue 169 by inserting a synthetic oligonucleotide into a restriction site on the lipocortin DNA sequence, thereby creating a codon for methionine at that site. We restricted pLipo8 with BglII and ligated into that site oligonucleotides Lipo 75 and 76 (see FIG. 20) using T4 ligase. These complementary oligonucleotides were constructed with sticky ends complementary to the cohesive ends of the BglII site for insertion into the plasmid. We transformed E.coli JA221 cells with this ligation mixture and selected transformants by growth on LB-ampicillin plate. We screened the transformants for those colonies containing the correct orientation of the inserted oligonucleotides by restriction mapping. One such colony, designated Lipo 9, was grown up in culture and its expressed protein extracted. The crude protein extract was treated with cyanogen bromide and subjected to SDS-polyacrylomide gel electrophoresis. A 17.7 Kd polypeptide fragment was produced and the extra amino acids introduced into the sequence by insertion of the synthetic oligonucleotides cleaved away (see FIG. 21).

Thus, we have isolated at least three biologically active lipocortin-like polypeptide fragments by the use of recombinant DNA techniques—the 26 Kd fragment of Lipo 8, the 14.6 Kd fragment of Lipo 11, and the 20.7 Kd fragment of Lipo 15. It is to be understood, however, that other lipocortin-like polypeptide fragments can be produced by the abovedescribed procedure (e.g., by replacement of other amino acids along the lipocortin amino acid sequence with methionine). Furthermore, lipocortin-like fragments can be produced by altering the DNA sequence encoding lipocortin to introduce or insert amino acids other than methionine to yield an altered polypeptide. This polypeptide can then be cleaved by an appropriate enzyme or chemical to yield biologically active fragments (e.g., cysteines can be inserted and the protein cleaved with NTCB, 2-nitro-5-thiocyanobenzoic acid).

ISOLATION OF A DNA SEQUENCE ENCODING N-LIPOCORTIN

We have also obtained a nucleotide sequence encoding a portion of N-lipocortin, a human lipocortin-like polypeptide displaying phospholipase $A_2$ inhibitory activity and having amino acid homology to the 37 Kd lipocortin produced according to this invention.

I. PURIFICATION OF LIPOCORTIN AND N-LIPOCORTIN FROM HUMAN PLACENTA

A fresh placenta was packaged on ice immediately after birth and processed within 6 h as follows: We skinned the placenta, cut it into cubes and washed the tissue with ten 300 ml changes of ice cold PBS (50 mM $Na_2HPO_4$, pH 7.2, 150 mM NaCl) and 5% sucrose until the tissue was pink and no additional hemoglobin was released by the washes. The washed placenta weighed about 350 g.

We washed 30 g of the placenta tissue with 150 ml of extraction buffer (25 mM Tris-HCl, pH 7.7, 5 mM EDTA, 0.1 mg/ml aprotinin, 0.1 mg/ml soybean trypsin inhibitor, and 40 uM pepstatin A) and then suspended the tissue in 100 ml of the same buffer. We disrupted the preparation with a polytron for 5–7 min on ice and subjected the homogenate to centrifugation at 4° C. for 15 min at 10,000 rpm in an SS34 rotor. We decanted the supernatants, disrupted the pellets with a polytron in an additional 100 ml of extraction buffer and subjected the suspension again to centrifugation at 10,000 rpm for 15 min. The supernatants of both extractions were combined and processed.

First, we subjected the extract to DEAE-cellulose chromatography on an 80 ml column (DE52, Whatman Ltd., column dimensions: 2.5 cm dia×16 cm) that had been equilibrated with 25 mM Tris-HCl (pH 7.7). We concentrated the flow-through preparations by ultrafiltration with an Amicon PM10 membrane to 15 ml. We then subjected the concentrated preparation to centrifugation for 15 min at 18,000 xg in an SS34 rotor. The apparent ionic strength of the concentrate was approximated by measuring the conductivity of the flow-through from the ultrafiltration. Based on this value, we diluted the concentrate with water to an apparent ionic strength equal to that of 25 mM Tris-HCl (pH 7.7) (10 ml of water was added). We next subjected this preparation to a second DEAE-cellulose step on a 40 ml column and further fractionated the DEAE-flow-through by gel filtration chromatography on a 200 ml P150 column (column dimensions: 2.5 cm dia×40 cm), which also was performed in 25 mM Tris-HCl (pH 7.7). We collected 5 ml fractions of this eluate and assayed an aliquot for phospholipase inhibitory activity using the in vitro assay described in Example A above. According to this assay, the eluate contained a single broad peak of inhibitory activity with an apparent molecular weight of 40 K as determined by gel filtration. We also characterized an aliquot of the eluate by SDS-polyacrylamide gel electrophoresis. This gel analysis indicated that the inhibitory activity in the eluate corresponded to a prominent protein band at 35 Kd. Western blotting analysis demonstrated that the 35 Kd band was immunoreactive with a rabbit antiserum against recombinant lipocortin produced in E.coli.

We next subjected the eluate from the gel filtration column to reverse phase high pressure liquid chromatography (HPLC) on a C4 column (Vydac), using a gradient of acetonitrile from 0–75% in 0.1% trifluoroacetic acid to elute the bound fragments. We found that the eluate actually contained two 35 Kd components: a natural human lipocortin component that eluted from the column with 65.8% acetonitrile and an N-lipocortin component that eluted with 65.1% acetonitrile. Only the natural lipocortin component was immunoreactive with the antibody raised against recombinant lipocortin.

Figure 23:
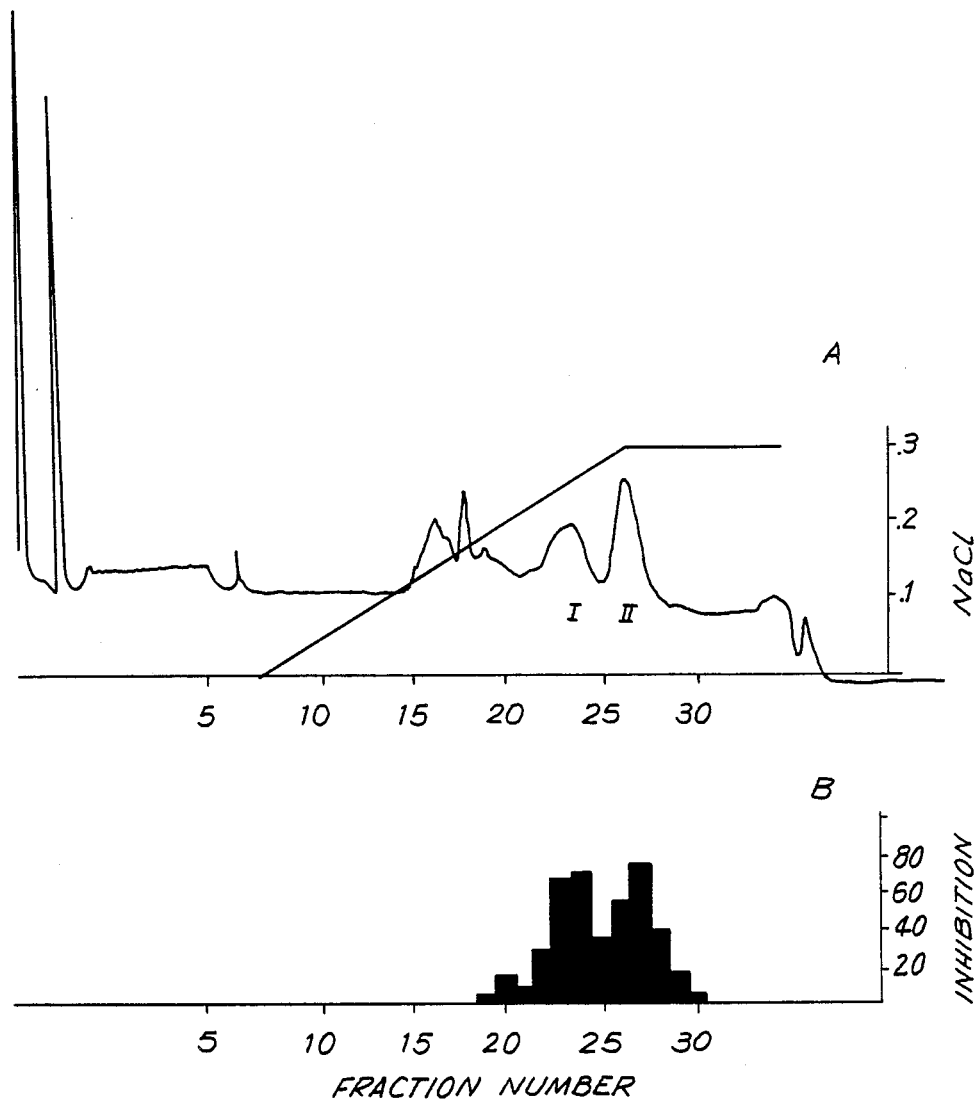
FIG. 23 depicts, in Panel A, the absorbance profile at 280 nm of lipocortin (peak I) and N-lipocortin (peak II) after fractionation via Mono S high resolution cation exchange chromatography. Panel B depicts the phospholipase $A_2$ inhibitory activity of the eluted lipocortin and N-lipocortin of the invention in % inhibition.

In order to further purify the two components in a manner in which we retained phospholipase $A_2$ inhibitory activity, we subjected the partially purified preparation from the gel filtration column to fast protein liquid chromatography (FPLC, Pharmacia) on a Mono S high resolution cation exchange chromatography resin (HR5/5, Pharmacia). At pH 6.0 in 50 mM MES buffer (2-morpholino-ethanesulfonic acid), both components bound to the Mono S column and were eluted with a gradient of NaCl. FIG. 23 shows the elution profile of the proteins (absorbance monitored at 280 nm) (panel A) and the profile of phospholipase $A_2$ inhibitory activity (panel B) from the Mono S column. In panel A, peak I corresponds to lipocortin and peak II to N-lipocortin. Only the material in peak I was immunoreactive with the rabbit antiserum against recombinant lipocortin. Panel B clearly indicates that both lipocortin and N-lipocortin show phospholipase $A_2$ inhibitory activity. Based on their relative amounts in the purified preparations, we estimate that the specific activities of the two proteins as phospholipase inhibitors are roughly identical.

We have also analyzed these two proteins by tryptic mapping. A larger portion of a placenta was processed and the proteins purified using the protocol as detailed above. The sizes and volumes of solutions and columns were adjusted appropriately. After the two 35 Kd proteins were separated by reverse phase HPLC, 100 μg of each of the purified proteins was subjected to tryptic mapping analysis as follows: We dried the appropriate HPLC fractions under vacuum in a Speed Vac Concentrator (Savant), resuspended the resulting pellets in 400 μl of 0.1 M ammonium bicarbonate (pH 8.0, 0.1 mM $CaCl_2$), and digested the mixture with trypsin. TPCK-trypsin (Worthington, 5 μg total) was added to 100 μg of protein and the digestion performed for 16 h at 37° C. The trypsin was added in three equal aliquots: the first at time zero, the second after 4 h, and the third after 12 h of incubation. The digest was acidified with formic acid to 20% (v/v).

Figure 24:
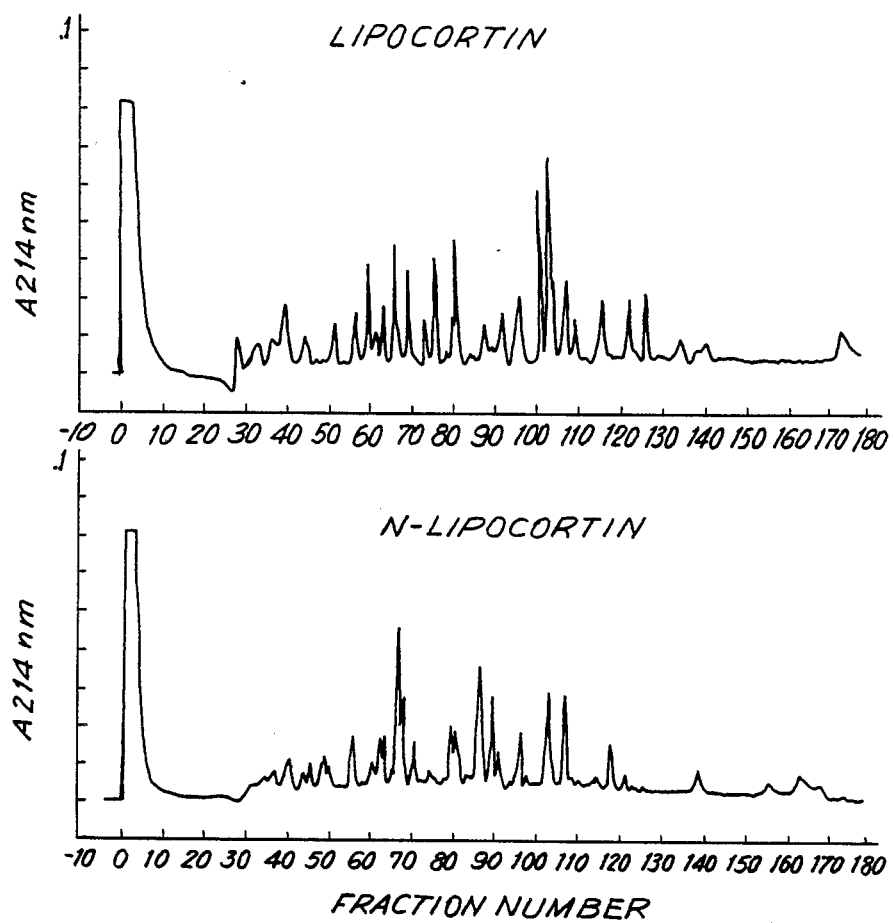
FIG. 24 depicts the tryptic maps of the lipocortin and N-lipocortin proteins isolated according to the methods of this invention.

We then resolved the cleavage fragments from the trypsin digestion by reverse phase high pressure liquid chromatography at 40° C. on a C18 column as described earlier in Example A. The column eluate was monitored at 214 nm. The tryptic maps for lipocortin (panel A) and N-lipocortin (panel B) are shown in FIG. 24. The tryptic map of the natural human lipocortin isolated from placenta is identical to the tryptic map obtained from the 37 Kd lipocortin derived from the expression of human macrophage cDNA. DNA sequence analysis revealed two amino acid differences between the placenta and macrophage-derived lipocortins. The map for N-lipocortin shows that protein to be unique.

We concentrated the eluate fractions corresponding to eleven of the peaks from the tryptic map of N-lipocortin on a Speed Vac Concentrator and subjected them to amino-terminal protein sequence analysis using a gas phase sequencer (Applied Biosystems 470A). PTH-amino acids from each cycle of the Edman degradation were analyzed by reverse phase high pressure liquid chromatography using the Applied Biosystems 120A PTH analyzer. The sequences derived from these analyses are shown in FIG. 25. (The "T" numbers to the left of the sequences in FIG. 25 correspond to the peak numbers which are shown on the column profile at the top of the figure.)

Most of the peptide sequences of N-lipocortin are unique, although some show sequence homology to human lipocortin purified in accordance with this invention, suggesting that the two 35 Kd components—lipocortin and N-lipocortin, respectively —may be derived from the same family of proteins. As shown in FIG. 25, to date, we have determined the primary structure of approximately one third of the N-lipocortin molecule. Since the sequences of those fragments derived from HPLC peaks containing multiple fragments can be determined using techniques known in the art, we have actually provided the data necessary to determine the primary structure of approximately 50% of the molecule.

J. SYNTHESIS OF OLIGONUCLEOTIDE PROBES FOR N-LIPOCORTIN PROTEIN SEQUENCES

Having determined the amino acid sequences of various regions of N-lipocortin from human placenta (see FIG. 25), we chemically synthesized four pools of antisense oligonucleotide DNA probes that coded for some of those protein sequences. We used the same strategy and procedure as detailed earlier in Example B for recombinant lipocortin. The amino acid sequences of the four selected regions of N-lipocortin and all the possible nucleotide codon combinations that encode them are shown in FIG. 26. Coding degeneracies are indicated as follows: N=C, T, A or G; R=A or G; Y=C or T; H=A, C or T, P=G or C; X=A, G or T; and Z=A or T.

As shown in FIG. 26, the four pools of DNA probes correspond to the amino acid sequences of tryptic fragments T20, T25, T24 and T9, respectively. To reduce further the degeneracies in the probes, we prepared each pool in subpools. Oligonucleotides NLip1 to NLip3, corresponding to the amino acid sequence of fragment T20, are 24-mers with 128 fold degeneracy. Oligonucleotides NLip4 to NLip7 are 18-mers with 32 fold degeneracy and are homologous to the amino acid sequence of fragment T25. Oligonucleotides NLip8 to NLip11 are 20-mers with 72 fold degeneracy, corresponding to the amino acid sequence of fragment T24, and NLip12 to NLip15 are 17-mers with 128 fold degeneracy, derived from the amino acid sequence of fragment T9.

To test if our synthetic probes actually recognized human sequences, we hybridized the 3 subpools, NLip1, NLip2, and NLip3, which were end-labeled with $^{32}P$ using $[\gamma]$-$^{32}$P-ATP and T4 polynucleotide kinase, to GeneScreen filters containing poly (A)+ mRNA from human placenta, utilizing the Northern blotting technique [H. Lehrach et al., supra]. Subpool NLip1 hybridized to an 1800 nucleotide mRNA which appears to be the same size as lipocortin mRNA.

K. CONSTRUCTION AND SCREENING OF A HUMAN PLACENTA cDNA LIBRARY

We constructed a human cDNA library from poly (A)+ mRNA isolated from human placenta using essentially the same procedure as described earlier in Example C for construction of the human macrophage cDNA library. In this embodiment, however, we extracted total RNA from the human placenta of a female fetus by the guanidine isothiocyanate method essentially as described by J. M. Chirgwin et al. [Biochemistry, 18, pp. 5294-99 (1979)]. This RNA preparation was enriched for poly (A)+ RNA by two passages over an oligo(dT)-cellulose column (PL Biochem) and used to synthesize double stranded cDNA sequences which were then inserted into λgt10 and amplified in *E.coli* C600 hfl cells.

We screened the human placenta cDNA library with the labeled oligonucleotide probe, NLip1, using nitrocellulose filters as described below. An overnight culture of C600 hfl cells in L broth and 0.2% maltose was pelleted and resuspended in an equal amount of SM buffer. We pre-adsorbed 0.9 ml of cells with $2\times10^6$ phage particles at room temperature for 15 min. We diluted the suspension to 50 ml in LB plus 10 mM MgSO$_4$ and 0.7% agarose at 55° C. and plated it on LB plates plus 10 mM MgSO$_4$. We screened 30 such plates. We incubated the plates at 37° C. for approximately 5 h and then chilled the plates at 4° C. for 1 h to allow the agarose to harden. We then transferred the λ phage particles from the plaque library plates to S&S nitrocellulose filters by placing the filters onto the plates containing the recombinant plaques for 5 min. We then lifted the filters from the plates, lysed the phages on the filters by placing the filters onto a pool of 0.5 N NaOH-1.5 M NaCl for 5 min and neutralized and submerged the filters in 1 M Tris-HCl-1.5 M NaCl (pH 7.0). The filters were then air-dried and baked at 80° C. for 2 h.

We prehybridized and hybridized the treated filters to the oligonucleotide probe, NLip1, in 0.2% polyvinylpyrrolidone (M.W. 40,000), 0.2% ficoll (M.W. 400,000), 0.2% bovine serum albumin, 0.05 M Tris-HCl (pH 7.5), 1M sodium chloride, 0.1% sodium pyrophosphate, 1% SDS, 10% dextran sulfate (M.W. 500,000) and denatured salmon sperm DNA ($\geq 100$ µg/ml) according to manufacturer's specifications (New England Nuclear) for Colony/Plaque Screen ™ membranes. We detected hybridizing cDNA sequences by autoradiography.

By means of this technique, we picked six positive plaques and rescreened at lower density using the same probe. We isolated the DNA of these clones, digested the DNA with EcoRI, and hybridized the sequences with the NLip1 probe using the Southern blot technique [E. M. Southern, supra]. The cDNA inserts of all six clones hybridized to the NLip1 probe.

We next restricted the DNA of these phages with EcoRI and isolated the cDNA inserts. Digestion of one of the clones, λ-Nlipo21-2, with EcoRI resulted in an approximately 500 base pair fragment which we subcloned into plasmid pUC9 to produce plasmid pNlip1. We sequenced this plasmid by the method of Maxam and Gilbert [A. M. Maxam and W. Gilbert, supra]. As depicted in FIG. 27, the plasmid carries a 394 base pair cDNA insert that contains 99 base pairs of the N-lipocortin coding sequence (corresponding to 33 amino acids), and 295 base pairs of the N-lipocortin 3' noncoding region, including a poly (A) addition site and an approximately 50 base pair poly (A) tail. The DNA coding sequence of N-lipocortin not only contains the sequence corresponding to the oligonucleotide probe derived from tryptic fragment T20, i.e., NLip1, but also the sequence corresponding to tryptic fragment T32 (see FIG. 25), thus confirming that we have cloned a portion of the gene encoding the N-lipocortin protein. This cDNA sequence as well as the oligonucleotide probes described in Example J can then be used as probes to screen for and isolate the DNA sequence encoding full length N-lipocortin.

Although clone λ-Nlipo21-2 contains the N-lipocortin DNA sequence encoding only a small region of the protein, the structural homology between lipocortin and N-lipocortin is borne out by this region. As shown in Table 4 below, 11 of the last 17 amino acids at the carboxyl terminus of the two proteins are identical. Of the five differences, most are conservative amino acid substitutions. Based on the similarity in the phospholipase A$_2$ inhibitory activity of the two proteins and the similarity in the protein and DNA sequences of the proteins, we conclude that N-lipocortin and lipocortin represent a family of related proteins.

TABLE IV

SEQUENCE HOMOLOGY AT C-TERMINUS OF LIPOCORTIN AND N-LIPOCORTIN

| | |
|---|---|
| LIPO: | GlnLysMetTyrGlyIleSerLeuCysGlnAlaIleLeu— |
| N-LIPO: | LysArgLys_TyrGly_Lys_SerLeu_TyrTyrTyrIleGln— |
| LIPO: | AspGluThrLysGlyAspTyrGluLysIleLeuValAla— |
| N-LIPO: | GlnAsp_ThrLysGlyAspTyr_GlnLys_AlaLeuLeuTyr— |
| LIPO: | LeuCysGlyGlyAsn |
| N-LIPO: | LeuCysGlyGlyAspAsp |

A comparison of the nucleotide sequences of the lipocortin and N-lipocortin of this invention shows approximately 60% homology (see FIG. 28).

Microorganisms and recombinant DNA sequences prepared by the processes described herein are exemplified by a culture deposited in the culture collection of In Vitro International, Inc., Ann Arbor, Mich. The culture was deposited on Jan. 8, 1986 and is identified as follows:

E.coli JA221(pNLip1):IVI No. 10093

IMPROVING THE YIELD AND ACTIVITY OF HUMAN LIPOCORTIN-LIKE POLYPEPTIDES PRODUCED IN ACCORDANCE WITH THIS INVENTION

The level of production of a protein is governed by three major factors: the number of copies of its gene within the cell, the efficiency with which those gene copies are transcribed and the efficiency with which they are translated. Efficiency of transcription and translation (which together comprise expression) is in turn dependent upon nucleotide sequences normally situated ahead of the desired coding sequence. These nucleotide sequences or expression control sequences define, inter alia, the location at which RNA polymerase interacts to initiate transcription (the promoter sequence) and at which ribosomes bind and interact with the mRNA (the product of transcription) to initiate translation. Not all such expression control sequences function with equal efficiency. It is thus of advantage to separate the specific lipocortin coding sequences of this invention from their adjacent nucleotide sequences and to fuse them instead to other known expression control sequences so as to favor higher levels of expression and production of lipocortin-like polypeptides. This having been achieved, the newly engineered DNA fragments may be inserted into higher copy number plasmids or bacteriophage derivatives in order to increase the number of gene copies within the cell and thereby further to improve the yield of expressed lipocortin-like polypeptides.

Several expression control sequences may be employed as described above. These include the operator, promoter and ribosome binding and interaction sequences (including sequences such as the Shine-Dalgarno sequences) of the lactose operon of E.coli ("the lac system"), the corresponding sequences of the tryptophan synthetase system of E.coli ("the trp system"), the major operator and promoter regions of phage λ ($O_L P_L$ as described above and $O_R P_R$), a control region of filamentous single-stranded DNA phages, the tac or trc system, the promoter for 3-phosphoglycerate kinase or other glycolytic enzymes, the promoters of acid phosphatase, e.g., Pho5, the promoters of the yeast α-mating factors, promoters for mammalian cells such as the SV40 early and late promoters, adenovirus late promoter and metallothionine promoter, and other sequences which control the expression of genes of prokaryotic or eukaryotic cells and their viruses or combinations thereof.

Therefore, to improve the production of the lipocortin-like polypeptides of this invention, the DNA sequences for those polypeptides may be prepared as before and inserted into a recombinant DNA molecule closer to its former expression control sequence or under the control of one of the above improved expression control sequences. Such methods are known in the art.

Other methods useful to improve the efficiency of translation involve the insertion of chemically or enzymatically prepared oligonucleotides in front of the initiating codon of the lipocortin-related DNA sequences of this invention or the replacement of codons at the N-terminal end of the DNA sequence with those chemically or enzymatically prepared oligonucleotides. By this procedure, a more optimal primary and higher order structure of the messenger RNA can be obtained. More specifically, a sequence can be so designed that the initiating AUG codon occurs in a readily accessible position (i.e., not masked by secondary structure) either at the top of a hairpin or in other single-stranded regions. The position and sequence of the aforementioned Shine-Dalgarno segment can similarly be optimized. The importance of the general structure (folding) of the messenger RNA has been documented (D. Iserentant and W. Fiers, "Secondary Structure Of mRNA And Efficiency Of Translation Initiation", Gene, 9, pp. 1–12 (1980)).

Further increases in the cellular yield of the lipocortin-like polypeptides of this invention may be achieved by increasing the number of genes that can be utilized in the cell. This may be achieved by insertion of the lipocortin gene (with or without its transcription and translation control elements) into a higher copy number plasmid or into a temperature-controlled copy number plasmid (i.e., a plasmid which carries a mutation such that the copy number of the plasmid increases after shifting the temperature (B. Uhlin et al., "Plasmids With Temperature-Dependent Copy Number For Amplification Of Cloned Genes And Their Products", Gene, 6, pp. 91–106 (1979)).

Alternatively, an increase in gene dosage can be achieved, for example, by insertion of recombinant DNA molecules, engineered in the manner described above, into the temperate bacteriophage λ, most simply by digestion of the plasmid with a restriction enzyme, to give a linear molecule which is then mixed with a restricted phage λ cloning vehicle (e.g., of the type described by N. E. Murray et al., "Lambdoid Phages That Simplify The Recovery Of In Vitro Recombinants", Mol. Gen. Genet. 150, pp. 53–61 (1977), and N. E. Murray et al., "Molecular Cloning Of The DNA Ligase Gene From Bacteriophage T4", J. Mol. Biol., 132, pp. 493–505 (1979)), and the recombinant DNA molecule produced by incubation with DNA ligase. The desired recombinant phage is then selected and used to lysogenize a host strain of E.coli.

Therefore, it should be understood that the lipocortin-like polypeptide coding sequences of this invention may be removed from the disclosed vectors and inserted into other expression vectors, as previously described (supra) and these vectors employed in various hosts, as previously described (supra) to improve the production of the human lipocortin-like polypeptides of this invention.

While we have hereinbefore presented a number of embodiments of this invention, it is apparent that our basic construction can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

We claim:

1. An essentially pure fragment of human lipocortin, selected from the group consisting of
   (a) Lipo-L
   (b) e-1,
   (c) e-2,
   (d) e-3,
   (e) e-4,
   (f) e-5,
   (g) the 26 Kd fragment of Lipo 8,
   (h) the 14.6 Kd fragment of Lipo 11, and
   (i) the 20.7 Kd fragment of Lipo 15.

2. A pharmaceutically acceptable composition useful in the treatment of arthritic, allergic, dermatologic, ophthalmic, and collagen diseases and other disorders involving inflammatory processes which comprise a pharmaceutically effective amount of at least one polypeptide selected from the group consisting of polypeptides according to claim 1.

3. A method for treating arthritic, allergic, dermatologic, ophthalmic, and collagen diseases and other disorders involving inflammatory processes which comprises administering a pharmaceutically effective amount of a composition according to claim 2.

4. A method for treating arthritic, allergic, dermatologic, ophthalmic, and collagen diseases and other disorders involving inflammatory processes which comprises administering a pharmaceutically effective amount of an N-lipocortin, the N-lipocortin having the following characteristics:
 (a) its ability to inhibit the enzyme phospholipase $A_2$,
 (b) comprising the tryptic fragments:
  (1) Leu,Tyr,Asp,Ser,Met,Lys;
  (2) Leu,Ser,Leu,Asn,Gly,Asp,Thr,Ser,Thr, Pro,-Pro,Ser,Ala,Tyr,Gly;
  (3) Ser,Leu,Tyr,Tyr,Tyr,Ile,Gln,Gln,Asp, Thr,Lys;
  (4) Trp,Ile,Ser,Ile,Met,Thr,Gla,Arg;
  (5) Ser,Tyr,Ser,Pro,Tyr,Asp,Met,Leu,Glu, Ser,Ile;
  (6) Leu,Leu,Val,Val,Tyr,Pro,X,Thr,Gln, Ile,Leu;
 wherein X is any amino acid, and
 (c) having a carboxy-terminus consisting of the amino acid sequence:
LysArgLysTyrGlyLysSerLeuTyrTyrIleGlnGlnAspThrLysGlyAsp TyrGlnLysAlaLeuLeuTyrLeuCysGlyGlyAspAsp, the N-lipocortin being selected from the group consisting of:
  (1) a mature N-lipocortin; and
  (2) a met-N-lipocortin.

5. A method for reducing inflammation which comprises administering a pharmaceutically effective amount of an N-lipocortin, the N-lipocortin having the following characteristics:
 (a) its ability to inhibit the enzyme phospholipase $A_2$,
 (b) comprising the tryptic fragments:
  (1) Leu,Tyr,Asp,Ser,Met,Lys;
  (2) Leu,Ser,Leu,Asn,Gly,Asp,Thr,Ser,Thr, Pro,-Pro,Ser,Ala,Tyr,Gly;
  (3) Ser,Leu,Tyr,Tyr,Tyr,Ile,Gln,Gln,Asp, Thr,Lys;
  (4) Trp,Ile,Ser,Ile,Met,Thr,Glu,Arg;
  (5) Ser,Tyr,Ser,Pro,Tyr,Asp,Met,Leu,Glu, Ser,Ile;
  (6) Leu,Leu,Val,Val,Tyr,Pro,X,Thr,Gln, Ile,-Leu;
 wherein x is any amino acid, and
 (c) having a carboxy-terminus consisting of the amino acid sequence, LysArgLysTyrGlyLysSerLeuTyrTyrTyrIle GlnGlnAspThrLysGlyAspTyrGlnLysAlaLeuLeuTyrLeuCysGlyGly AspAsp; the N-lipocortin being selected from the group consisting of:
  1. a mature N-lipocortin; and
  2. a met-N-lipcocortin.

* * * * *

UNITED STATES PATENT AND TRADEMARK OFFICE
CERTIFICATE OF CORRECTION

PATENT NO. : 4,950,646

DATED : August 21, 1990

INVENTOR(S) : Barbara P. Wallner, R. Blake Pepinsky, Jeffrey L. Garwin, Daniel G. Schindler, Kuo-Sen Huang It is certified that error appears in the above-identified patent and that said Letters Patent is hereby corrected as shown below:

In the drawings, Sheet 4, Fig. 4, amino acids should not appear beneath nucleotides 1-51, which are not part of the coding sequence.

Column 25, line 23, after "IVI No. 10042", insert -- This deposit was transferred to the American Type Culture Collection, Rockville, Maryland, on June 20, 1991, where it is now available under accession number ATCC 68812. --;
        line 28, after "IVI No. 10046", insert -- This deposit was transferred to the American Type Culture Collection, Rockville, Maryland, on June 20, 1991, where it is now available under accession number ATCC 68763. --;
        line 29, after "IVI No. 10088.", insert -- This deposit was transferred to the American Type Culture Collection, Rockville, Maryland, on June 20, 1991, where it is now available under accession number ATCC 74106. --.

Column 36, line 60, after "IVI No. 10093", insert -- This deposit was transferred to the American Type Culture Collection, Rockville, Maryland, on June 20, 1991, where it is now available under accession number ATCC 68811. --

Signed and Sealed this

Twelfth Day of April, 1994

*Attest:*

BRUCE LEHMAN

*Attesting Officer*

Commissioner of Patents and Trademarks